United States Patent
Wang et al.

(10) Patent No.: US 11,602,532 B2
(45) Date of Patent: Mar. 14, 2023

(54) NANOPARTICLE FORMULATIONS OF DECOQUINATE IN THE FORM OF SOLID SOLUTION

(71) Applicant: CAS Lamvac (Guangzhou) Biomedical Technology Co., Ltd., Guangzhou (CN)

(72) Inventors: Hongxing Wang, Guangzhou (CN); Shuanghong Liang, Guangzhou (CN); Yinzhou Fan, Guangzhou (CN); Zhenping Huang, Guangzhou (CN); Siting Zhao, Guangzhou (CN); Li Qin, Guangzhou (CN); Xiaoping Chen, Guangzhou (CN)

(73) Assignee: CAS Lamvac (Guangzhou) Biomedical Technology Co., Ltd., Guangzhou (CN)

( * ) Notice: Subject to any disclaimer, the term of this patent is extended or adjusted under 35 U.S.C. 154(b) by 320 days.

(21) Appl. No.: 16/971,934

(22) PCT Filed: Jan. 2, 2019

(86) PCT No.: PCT/CN2019/070099
§ 371 (c)(1),
(2) Date: Aug. 21, 2020

(87) PCT Pub. No.: WO2020/140197
PCT Pub. Date: Jul. 9, 2020

(65) Prior Publication Data
US 2021/0077480 A1  Mar. 18, 2021

(51) Int. Cl.
| | |
|---|---|
| *A61K 31/47* | (2006.01) |
| *A61P 33/06* | (2006.01) |
| *A61K 9/00* | (2006.01) |
| *A61K 47/10* | (2017.01) |
| *A61K 47/32* | (2006.01) |
| *A61K 47/38* | (2006.01) |
| *A61K 47/44* | (2017.01) |
| *B82Y 5/00* | (2011.01) |
| *B82Y 40/00* | (2011.01) |

(52) U.S. Cl.
CPC ............ *A61K 31/47* (2013.01); *A61K 9/0053* (2013.01); *A61K 47/10* (2013.01); *A61K 47/32* (2013.01); *A61K 47/38* (2013.01); *A61K 47/44* (2013.01); *A61P 33/06* (2018.01); *B82Y 5/00* (2013.01); *B82Y 40/00* (2013.01)

(58) Field of Classification Search
CPC ..................................................... A61K 31/47
See application file for complete search history.

(56) References Cited

U.S. PATENT DOCUMENTS

| | | | |
|---|---|---|---|
| 10,265,270 B2 * | 4/2019 | Wang | A61K 9/146 |
| 2017/0360708 A1 * | 12/2017 | Wang | A61K 9/146 |

FOREIGN PATENT DOCUMENTS

| | | |
|---|---|---|
| CN | 101564376 A | 10/2009 |
| CN | 104906044 A | 9/2015 |
| CN | 106667898 A | 5/2017 |
| CN | 107427504 A | 12/2017 |

OTHER PUBLICATIONS

International Search Report issued in corresponding International Application No. PCT/CN2019/070099, dated Oct. 9, 2019, 2 pages.

* cited by examiner

*Primary Examiner* — Rei Tsang Shiao
(74) *Attorney, Agent, or Firm* — Fish & Richardson P.C.

(57) ABSTRACT

Hot-melt extrusion for producing solid solution comprising nanoparticle formulation of decoquinate is disclosed. Aqueous phase comprising the nanoparticles of hot-melt extruding products is homogeneous and stable. Provided is the composition comprising the solid solution of decoquinate and a method of hot-melt extrusion for producing this composition comprising the solid dispersion of decoquinate. Furthermore, provided is the solid solution comprising nanosized decoquinate formulation having improved water solubility and enhanced delivery of decoquinate in digestive system for absorption, increasing bioavailability, and the efficacy against malaria at the liver stage.

13 Claims, 18 Drawing Sheets

Figure 13: F8 Decoquinate in HPLC Analysis

Figure 14: Decoquinate (API) HPLC Peak

Figure 15: Decoquinate (API) After Acid (pH=1.2) Solution Treatment for 2 Days

Figure 16: F8 Decoquinate After Acid (pH=1.2) Solution Treatment for 10 Days

Figure 17: F8 Decoquinate After Base (pH=9) Solution Treatment for 10 Days

NANOPARTICLE FORMULATIONS OF DECOQUINATE IN THE FORM OF SOLID SOLUTION

CROSS-REFERENCE TO RELATED APPLICATION

This application is a U.S. national phase filing under 35 U.S.C. § 371 of International Application No. PCT/CN2019/070099, filed Jan. 2, 2019, the contents of which are incorporated herein by reference in their entirety.

FIELD OF THE INVENTION

The present invention relates to a thermal heat process in a twin-screw extruder to extrude an extrudate in the form of solid solutions comprising the antimalarial (antiparasitic) agent decoquinate (also abbreviated as "DQ") or other therapeutic drugs such as other antiparasitic agents. In some embodiments, the solid solutions are in the form of a complex comprising the drug, a hot-melt extrudable excipient, and a small percentage of a plasticizer or solubilizer based on the weight of the complex. Examples of hot-melt extrudable excipients include hydroxypropyl methylcellulose, dimethylaminoethyl methacrylate copolymer, polyvinyl caprolactam-polyvinyl acetate-polyethylene glycol graft copolymer, and vinylpyrrolidone-vinyl acetate copolymer. These solid solutions are designed to act as solid oral dosages that will deliver an active pharmaceutical ingredient (API) in vivo to prevent or treat malarial infection or other parasitic diseases or disorders.

BACKGROUND OF THE INVENTION

Malaria is a mosquito-borne infectious disease caused by the infection of Plasmodium (vivax, malariae, falciparum, and ovale). Another species, Plasmodium knowlesi, however, can infect both humans and monkeys. The disease is most commonly transmitted by an infected female Anopheles mosquito. The mosquito bite introduces the parasites from the mosquito's saliva into a person's blood [Malaria Fact Sheet. No. 94. Updated March 2014, Retrieved 28 Aug. 2014]. The parasites travel to the liver where they mature and reproduce. Most deaths are caused by P. falciparum while P. vivax, P. ovale, and P. malariae generally cause a milder form of malaria. The mortality of severe cases caused by P. falciparum is extremely high, of which more than 70 percent are children under the age of 5. Travelers to the epidemic areas of malaria are also susceptible to the infection of the parasites. Plasmodium vivax and Plasmodium ovale are closely related and have unique biology which is generation of hypnozoites in the liver stage. The hypnozoites, the dormant liver stages, causes relapsing human malaria.

During the first 48 hours of Plasmodium infection in humans, primates, and rodents (the pre-erythrocyte stage), replication occurs in the liver while in later stages, Plasmodium replication occurs in the erythrocytes. Artemisinin is the most commonly used first-line antimalarial drug and used as the core drug of the artemisinin-based combination therapy (ACT). This medication and most of the classic anti-malarial medications such as chloroquine and quinine act during the erythrocyte stage but do not inhibit the growth of parasites at the liver stage. Resistance of Plasmodium to current antimalarial drugs has emerged worldwide. For example, chloroquine-resistant P. falciparum has spread to most malarial areas, and Plasmodium resistance to artemisinin has become a problem in some parts of Southeast Asia. ["Malaria Fact sheet N° 94". WHO. March 2014. Retrieved 28 Aug. 2014]. The extensive Plasmodium resistance to chloroquine and sulfadoxine/pyrimethamine and also resistance to the artemisinin component of ACT has become the key challenge of malaria control (Ariel, F. et al., A molecular marker of artemisinin-resistant Plasmodium falciparum malaria, Nature 505, 50-55, 2014). The hypnozoites of P. vivax and P. ovale infection in the dormant liver stage also make it difficult to control the disease. Primaquine, an antimalarial drug used for the liver stage, has serious side effects. It can sometimes cause acute hemolytic anemia in the patients with glucose-6-phosphate dehydrogenase deficiency (G6PDD). Malarone®, composed of atovaquone and proguanil, also inhibits the liver stage of Plasmodium parasites. The drug, however, is not considered cheap for the most patients who suffer from malaria. Thus new, efficient, and affordable anti-malarial drugs with low-toxicity, and especially with activity at the liver stage and lack of resistance by the parasite, are needed to protect susceptible populations.

Decoquinate (DQ, CAS No. 18507-89-6) has been found to have a potent inhibitory and killing effect against Plasmodium both in vitro and in vivo (Meister, S. et Al., Imaging of Plasmodium liver stages to drive next-generation antimalarial drug discovery, Science 2011; 334: 1372-7). With respect to the efficacy against Plasmodium liver stages as well as blood stages, that consequently prevents clinical symptoms, decreases transmission, and reduces the propensity for drug resistance development, decoquinate has prominent advantages over the existing anti-malarial drugs (da Cruz, F P. Et al., Drug Screen Targeted at Plasmodium Liver Stages Identifies a Potent Multistage Antimalarial Drug J Infect Dis (2012) 205 (8): 1278-1286). It interacts with and inhibits the cytochrome bc1 complex of Plasmodium mitochondria but does not affect mammalian respiratory chain. Decoquinate has been found to be safe as a veterinary drug and as a nanoparticle form in animal toxicity studies (Wang, H. et al., Nanoparticle formulations of decoquinate increase antimalarial efficacy against liver stage Plasmodium infections in mice, Nanomedicine: Nanotechnology, Biology, Medicine 10 (2014) 57-65). It does not have resistance from chloroquine-resistant Plasmodium (CN104906044A [2015]: a decoquinate nano-formulation and its preparation and application; da Cruz, F P. Et al., Drug Screen Targeted at Plasmodium Liver Stages Identifies a Potent Multistage Antimalarial Drug J Infect Dis (2012), 205(8): 1278-1286). Decoquinate has great potential to become an antimalarial drug. However, in order to develop an oral dosage form of decoquinate for clinical administration, the key issue of the solubility should be addressed and the dosage formulation should be made for the effective absorption of decoquinate by the intestine, therefore enabling the compound to become available and active in the body.

The hot-melt extrusion (HME) method has an advantage to solve the insolubility problem of chemical molecules by the utilization of controllable temperature at a serial of vessel segments, low melting point excipients, efficiency of physical interaction of ingredients, and mechanical preparation process. Nonetheless, to obtain HME product for poorly soluble compounds that is homogeneous and well dispersed in water phase and stable before reaching the intestine for absorption, excipients appropriate for the API and process parameters suitable for the compositions of formulation are essential requirements.

When the API is dispersed in the solid excipients as crystalline or amorphous particles, the solid dispersion is obtained. If the API is molecularly dissolved in the solid matrix constituted by excipients, the formulation may be the true solid solution. In the case of the true solid solution, the formulation is thermodynamically stable as the API and excipients are completely miscible with each other over the whole composition range. However, in a majority of cases, the API and excipients are miscible over a limited range, resulting in other solid solutions and dispersions which can encounter various instabilities. API initially dissolved in supersaturated solid solutions can precipitate over time because there is no driving force for solubilizing the API that diffuses to the surface of supersaturated solid solutions. The size distribution of API particles in solid dispersions can evolve over time as large particles grow at the expense of the smaller ones (Ostwald ripening). The number of small particles of API in suspension is gradually reduced and large particles are continuously increasing. API dispersed in amorphous particles are also thermodynamically unstable and can crystallize over time.

SUMMARY OF THE INVENTION

A thermal heat process is disclosed for preparing a solid solution formulation containing a pharmacologically active agent comprising the steps of mixing decoquinate with a hot-melt extrudable excipient, a plasticizer, or solubilizer to form a mixture. Processing said mixture is formed in a twin-screw extruder with multiple temperature zones at a hot-melt temperature less than the degradation temperature of decoquinate. Extruding said mixture forms an extrudate, wherein said decoquinate in said extrudate is in a solid solution. The solid solution provides a therapeutic drug that is active and can be further fabricated as solid oral dosage forms to release the therapeutic drug in vivo to prevent or treat malarial infection or other parasitic diseases or disorders.

The present invention provides a composition for HME, wherein the composition comprises, by dry weight, 5% to 30% of decoquinate, 60% to 90% of hot-melt extrudable excipients, and 5% to 10% of a plasticizer or a solubilizer.

In one embodiment, hot-melt extrudable excipients are hydroxypropyl methylcellulose (AFFINISOL™ HPMC HME), hydroxypropyl methyl cellulose acetate succinate (AFFINISOL™ HPMCAS), dimethylaminoethyl methacrylate copolymer (EUDRAGIT®EPO), polyvinyl caprolactam-polyvinyl acetate-polyethylene glycol graft copolymer (Soluplus®), vinylpyrrolidone-vinyl acetate copolymers (Kollidon® VA 64), polyethylene glycol, or a combination of two or more thereof.

In another embodiment, AFFINISOL™ HPMC HME, a commercial product designed to enhance the solubilization and inhibit the recrystallization of APIs and as a carrier of solid solution of API, it has a minimal hygroscopicity in contrast to other commercially available polymers used in HME; AFFINISOL™ HPMCAS is a soluble polymer that can help optimize solubility enhancement by maintaining stable solid dispersions and inhibiting API crystallization; the methacrylate copolymer EUDRAGIT®EPO (EPO) has an average molar mass (Mw) weight of approximately 47,000 g/mol. EPO has shown to dramatically enhance solubilization of acidic drugs via ionic interactions and by multiple hydrophobic contacts with polymeric side chains. The hydrophobic interactions could also play a role for solubilization of compounds that are not limited to acidic compounds. Soluplus® is a matrix copolymer with an amphiphilic chemical structure, used herein for making solid solutions as well as for enhancing the solubility of poorly soluble compounds in aqueous media; Kollidon® VA 64 is a matrix copolymer for solid dispersion applications due to its amphiphilic nature and has a wetting property, and facilitates the redissolution of solid dispersion.

In another embodiment, said polyethylene glycol is polyethylene glycol 8000, polyethylene glycol 6000, or polyethylene glycol 4000; the polyethylene glycol is used as a plasticizer to reduce the melting temperature in the melting process, thereby to reduce the chance of decoquinate degradation. In addition, polyethylene glycol may also increase the dissolution rate of the active ingredient decoquinate (PCT150162PPC).

In another embodiment, the plasticizer is any one of poloxamer 188 (Kolliphor® P188), polyoxyl 40 hydrogenated castor oil (RH 40), polyethylene glycol glyceryl stearate (Gelucire® 50/13), or polyethylene glycol glyceryl laurate (Gelucire® 44/14), or a combination of two or more thereof; the plasticizer is a pharmaceutical formulation excipient that can be used as solubilizer or emulsifier for enhancing the water solubility of the poorly soluble compound such that the active ingredient decoquinate is dispersed therein in the state of a molecule or a very fine particle, thereby facilitating the enhancement of the water solubility of decoquinate. The plasticizers have a low melting point and may enable the melting temperature range to be reduced accordingly during the melting process of the composition such that inter-component cohesion of the formulation can occur at lower temperatures than in the absence of plasticizers, thereby facilitating the formation of a solid solution of decoquinate with uniform density.

In addition, the polymer material used in the present invention may have thermoplastic behavior, high thermal stability, no toxicity, and the role of solubility enhancement. The selected solubilizers in the present invention are designed as formulation excipients used for HME process and are generally recognized as safe (GRAS) for clinical use.

The present invention provides HME preparation method of processing an HME composition, wherein a solid solution of decoquinate is produced.

The present invention provides an application of the solid solution of decoquinate as a pharmaceutical formulation for prevention and/or treatment of a disease caused by *Plasmodium* parasites.

Preferably, said disease refers to one or more of the following *Plasmodium* malaria caused by *Plasmodium vivax, Plasmodium falciparum, Plasmodium malariae, Plasmodium ovale,* and *Plasmodium knowlesi*.

The solid solution of decoquinate can be prepared into oral dosage forms such as tablets, granules, and filled capsules, if desired.

DETAILED DESCRIPTION OF THE INVENTION

Figure 1:
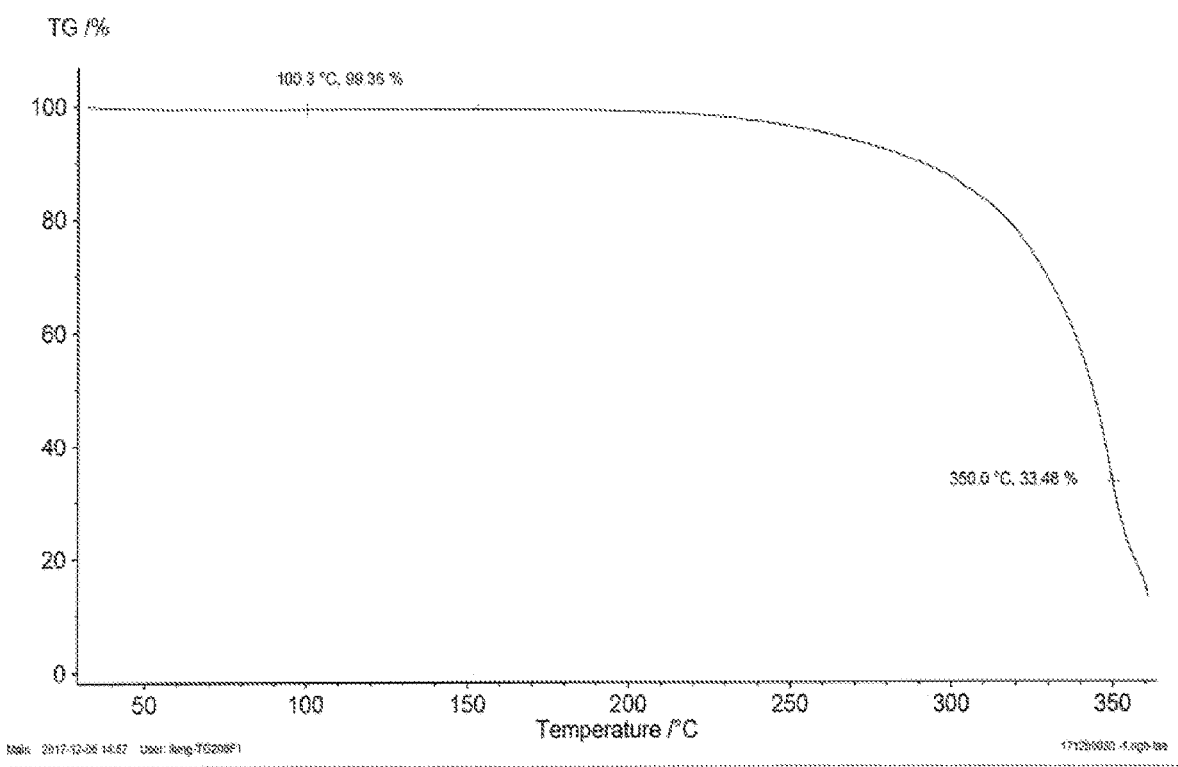
FIG. 1 shows the graph of thermogravimetric analysis of HME product made in Example 8 (F8). The amount of decoquinate was basically unchanged at a temperature below 250° C. and only began to decompose gradually at a temperature range from 250° C. to 350° C.

A thermal heat process is disclosed for preparing a solid solution formulation containing a pharmacologically active agent comprising the steps of mixing decoquinate with a hot-melt extrudable excipient, a plasticizer, or solubilizer to form a mixture.

Decoquinate and Other Antiparasitic Agents

The oral formulation compositions of the present invention comprise antiparasitic agents such as decoquinate, or mixtures of such agents.

Decoquinate (DQ), a (hydroxyl) quinoline, is produced by chemical synthesis. Its nomenclature is 4-hydroxyquinoline (ethyl-6-decyloxy-7-ethoxy-4-hydroxyquinoline-3-carboxylate) with CAS number 18507-89-6, molecular weight 418 g/mol, and the molecular formula C25H35NO5). Decoquinate corresponds to the following chemical structure:

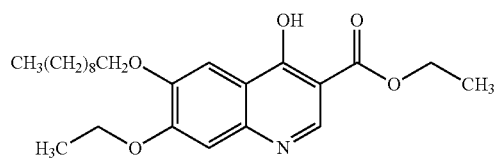

Decoquinate has a secondary amine functionality and can be used or formulated in its free base form. Alternatively, pharmaceutically acceptable salts of decoquinate can be used. Also, the anhydrous and various hydrate forms of decoquinate and its salts are contemplated within the scope of the invention.

The present invention provides a composition for HME, wherein the composition comprises, by dry weight, 5% to 30% of decoquinate, 60% to 90% of hot-melt extrudable excipients, 5% to 10% of a plasticizer or a solubilizer.

In one embodiment, the polymeric carrier materials are hydroxypropyl methylcellulose (AFFINISOL™ HPMC HME), hydroxypropyl methyl cellulose acetate succinate (AFFINISOL™ HPMCAS), dimethylaminoethyl methacrylate copolymer (EUDRAGIT®EPO), polyvinyl caprolactam-polyvinyl acetate-polyethylene glycol graft copolymer (Soluplus®), vinylpyrrolidone-vinyl acetate copolymers (Kollidon® VA 64), polyethylene glycol or a combination of two or more thereof.

In another embodiment, AFFINISOL™ HPMC HME, a commercial product designed to enhance the solubilization and inhibit the recrystallization of APIs and as a carrier of solid solution of API, has a minimal hygroscopicity in contrast to other commercially available polymers used in HME. All three subtypes of AFFINISOL™ HPMC HME can be used for decoquinate solid dispersion regardless of dissolution rate and efficacy of HME products. AFFINISOL™ HPMCAS is a soluble polymer that can help optimize solubility enhancement by maintaining stable solid dispersions and inhibiting API crystallization. There are also three subgroups of this product category according to the numbers of acetate and succinate substitution in the molecule. The product series are made by the commercial companies in different countries (Table 3). The effects of each subtype of HPMCAS on decoquinate solid dispersion were tested and compared in the respect of solubility enhancement and formulation stability. Although in vitro dissolution studies showed that the rank order of drug dissolution rate in solid dispersion being Kollidon® VA 64 and EUDRAGIT®EPO was greater than HPMC, in vivo investigations found that in the drug solid dispersion, HPMC and Kollidon® VA 64 had lower mean AUC 0-12 hours and lower Cmax than EUDRAGIT®EPO. The contradiction between in vivo and in vitro data may be due to the pH-dependence of EUDRAGIT®EPO. In the media of 0.1N hydrochloric acid and 0.05% (w/v) sodium dodecyl sulfate (SDS), the solid dispersion with EUDRAGIT®EPO dissolved significantly faster than the other formulations (Zheng, X., et al., Part II: Bioavailability in beagle dogs of nimodipine solid dispersions prepared by hot-melt extrusion. Drug Development & Industrial Pharmacy, 2007, 33, 783-789). Soluplus® is a matrix copolymer with an amphiphilic chemical structure, used herein for making solid solution as well as for enhancing the solubility of poorly soluble compounds in aqueous media. This polymer for decoquinate solid dispersion has been documented previously and demonstrated ideal characteristic feasibility for decoquinate HME (CN2015/096689 Dec. 8, 2015). Kollidon® VA 64 is a matrix polymer for solid dispersion applications due to its amphiphilic nature and has a wetting property and facilitates the redissolution of solid dispersion. It has a suitable physical ability of holding decoquinte in the HME composition as well as an improved dissolution rate of the API, as described in the previous documentation (CN2015/096689 Dec. 8, 2015).

In another embodiment, said polyethylene glycol is polyethylene glycol 8000, polyethylene glycol 6000 or polyethylene glycol 4000; the polyethylene glycol is used as a plasticizer to reduce the melting temperature in the melting process, thereby to reduce the chance of decoquinate degradation. In addition, polyethylene glycol increases the dissolution rate of decoquinate, and may improve the release and absorption of API in the digestive track.

In another embodiment, the plasticizer is any one of poloxamer 188 (Kolliphor® P188), polyoxyl 40 hydrogenated castor oil (RH 40), polyethylene glycol glyceryl stearate (Gelucire® 50/13), or polyethylene glycol glyceryl laurate (Gelucire® 44/14), or a combination of two or more thereof; the plasticizer herein is a pharmaceutical formulation excipient and also a solubilizer for enhancing the water solubility of the poorly soluble compound such that the active ingredient decoquinate is dispersed therein in the state of a molecule or a very fine particle, thereby facilitating the enhancement of the water solubility of decoquinate. In the process of hot melt extrusion, the solubilizers can act as plasticizers that have a low melting point, which may enable the melting temperature range to shift towards the lower level accordingly during the melting process of the composition such that inter-component cohesion of the formulation can occur at a lower temperature than in the absence of solubilizers, thereby facilitating the formation of a solid dispersion of decoquinate with uniform density.

The present invention provides a preparation method for HME compositions, wherein a solid solution of decoquinate is produced.

In a particular embodiment, the hot-melt extrusion (HME) is carried out in a hot-melt extruder, wherein the composition as described above is mixed inside a corotating twin-screw extruder with intermeshing, wherein each component of composition is mixed in the melting state in the horizontally split barrel of the machine with preset temperatures in each segmented screw, pressed through by twin screw extrusion, and shaped by die molding; the extruded material is allowed to cool down automatically at room temperature and comes out as stripped or other shapes of solid mixture, depending on the die. The stripped solid mixture is cut and pulverized into the powder of decoquinate solid solution.

In a preferred embodiment, the temperature of hot-melt extrusion is 50-200° C., preferably 120-180° C.; the screw rotation speed of the hot-melt extruder is 15-300 rpm, preferably 25 to 150 rpm.

In the preparation of the solid solution of decoquinate, it is necessary to adjust the melting temperature based on the composition of the raw materials so that not only the active ingredient decoquinate is effectively mixed with the hot-melt extrudable excipients at the molecular level, but also avoided is the thermal decomposition of decoquinate and excipients.

Figure 14:
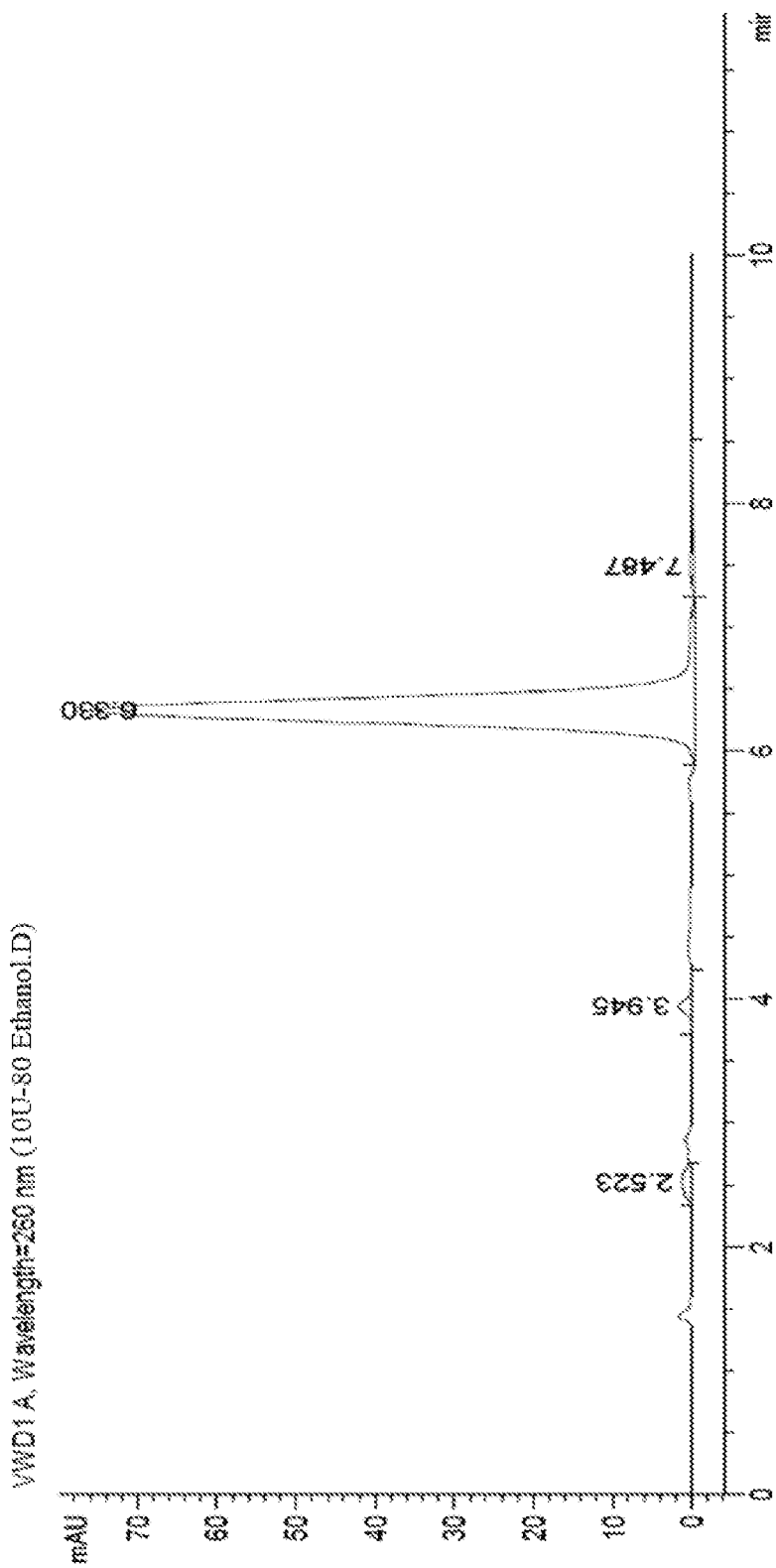
FIG. 14 is a HPLC graph of standard decoquinate dissolved in ethanol and diluted to a concentration in an appropriate range to show the peak pattern and the retention time of decoquinate in the established HPLC method.
Figure 15:
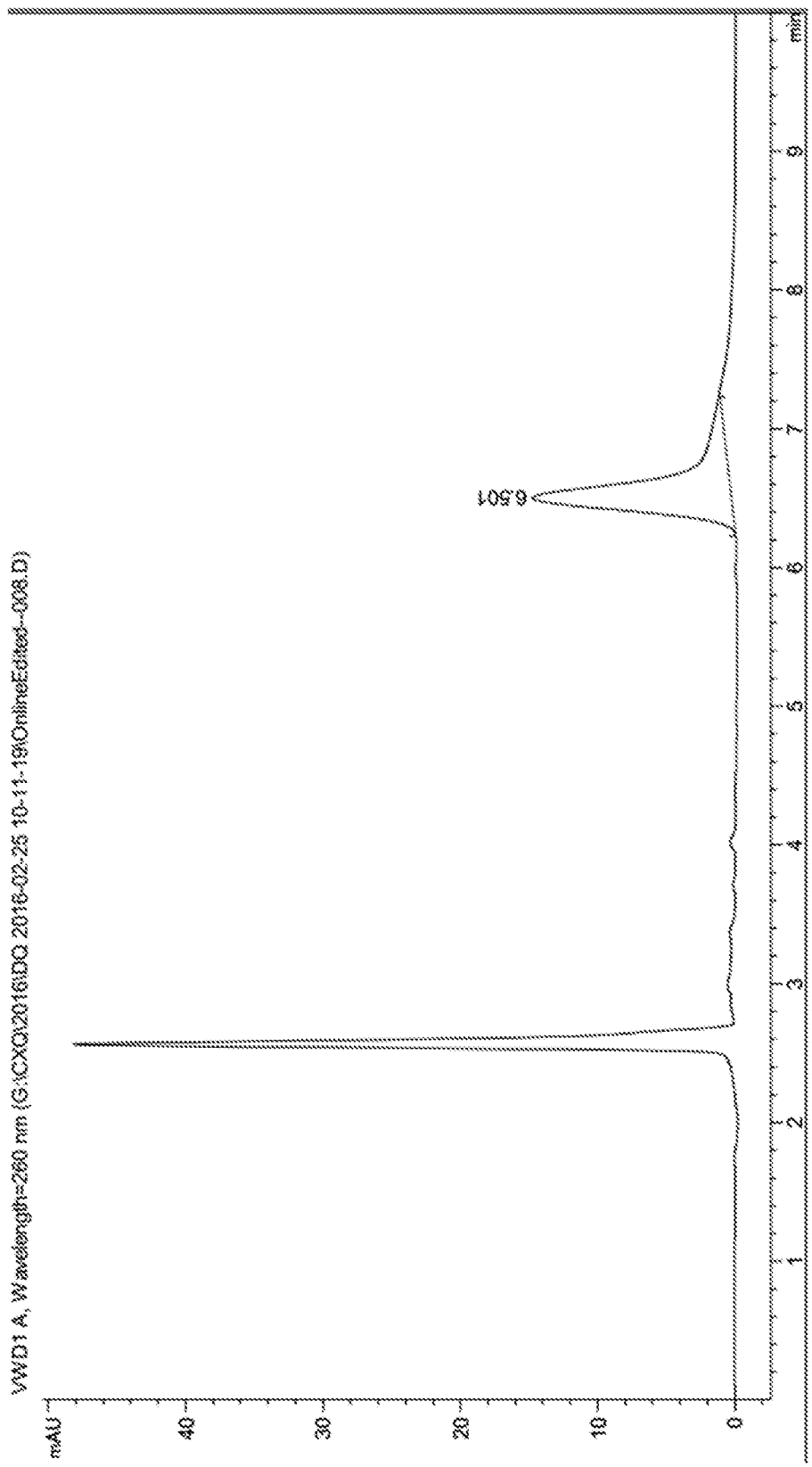
FIG. 15 shows the HPLC graph of standard decoquinate treated with pH 1.2 solution for 2 days. Samples are dialyzed against distilled water, diluted and analyzed with the established method. The treatment of pure decoquinate with acid solution caused the change in the peak pattern and the shift in the retention time of dominant peak.
Figure 16:
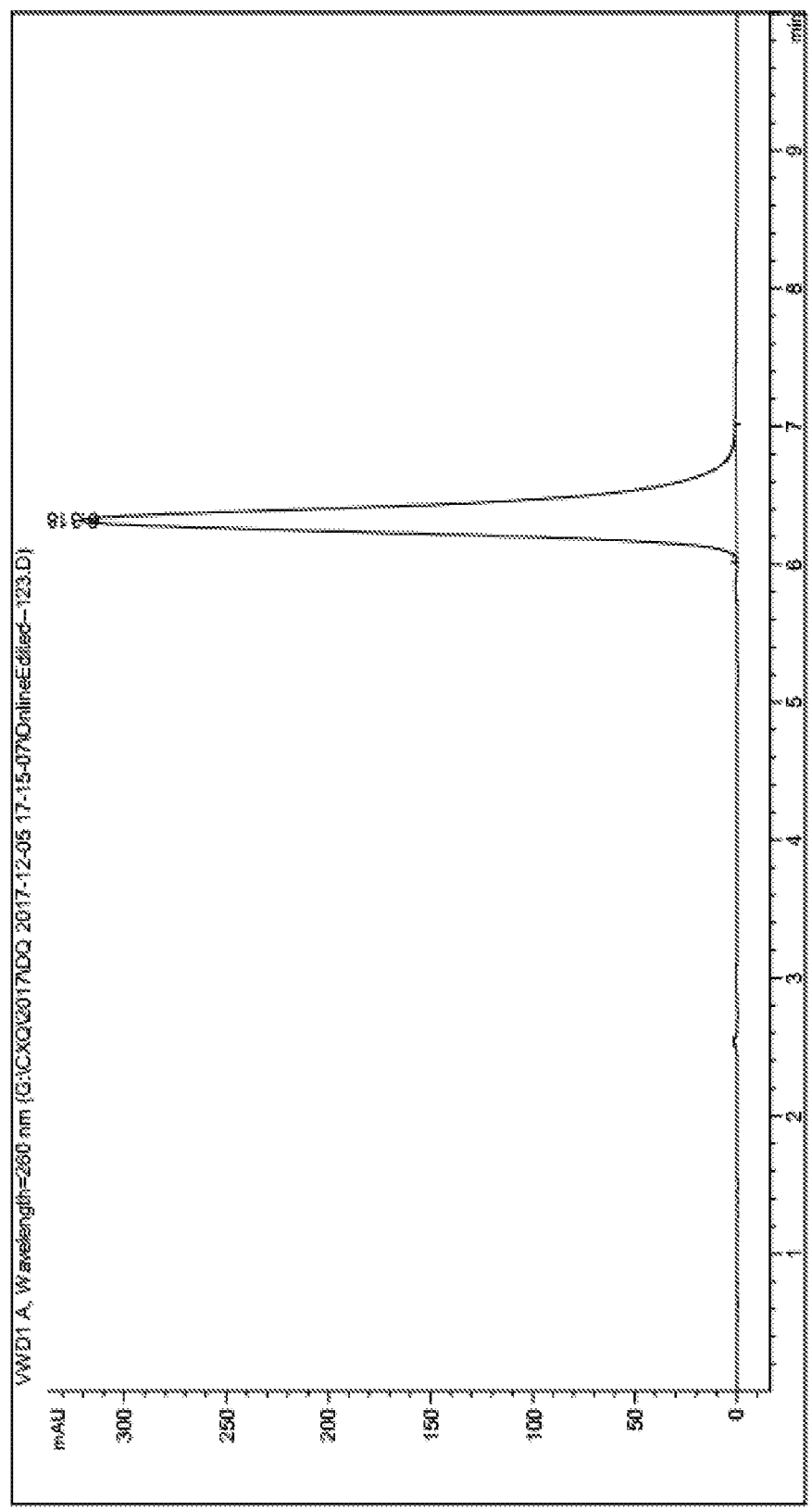
FIG. 16 shows that the solid solution prepared in Example 8 (F8) by the HME technique was treated with pH 1.2 solution for 10 days and the mixture was dialyzed, diluted and analyzed with the established HPLC method. The HPLC graph shows that decoquinate is not altered in either the peak pattern or the retention time of decoquinate in the HPLC analysis after the treatment with acid solution.
Figure 17:
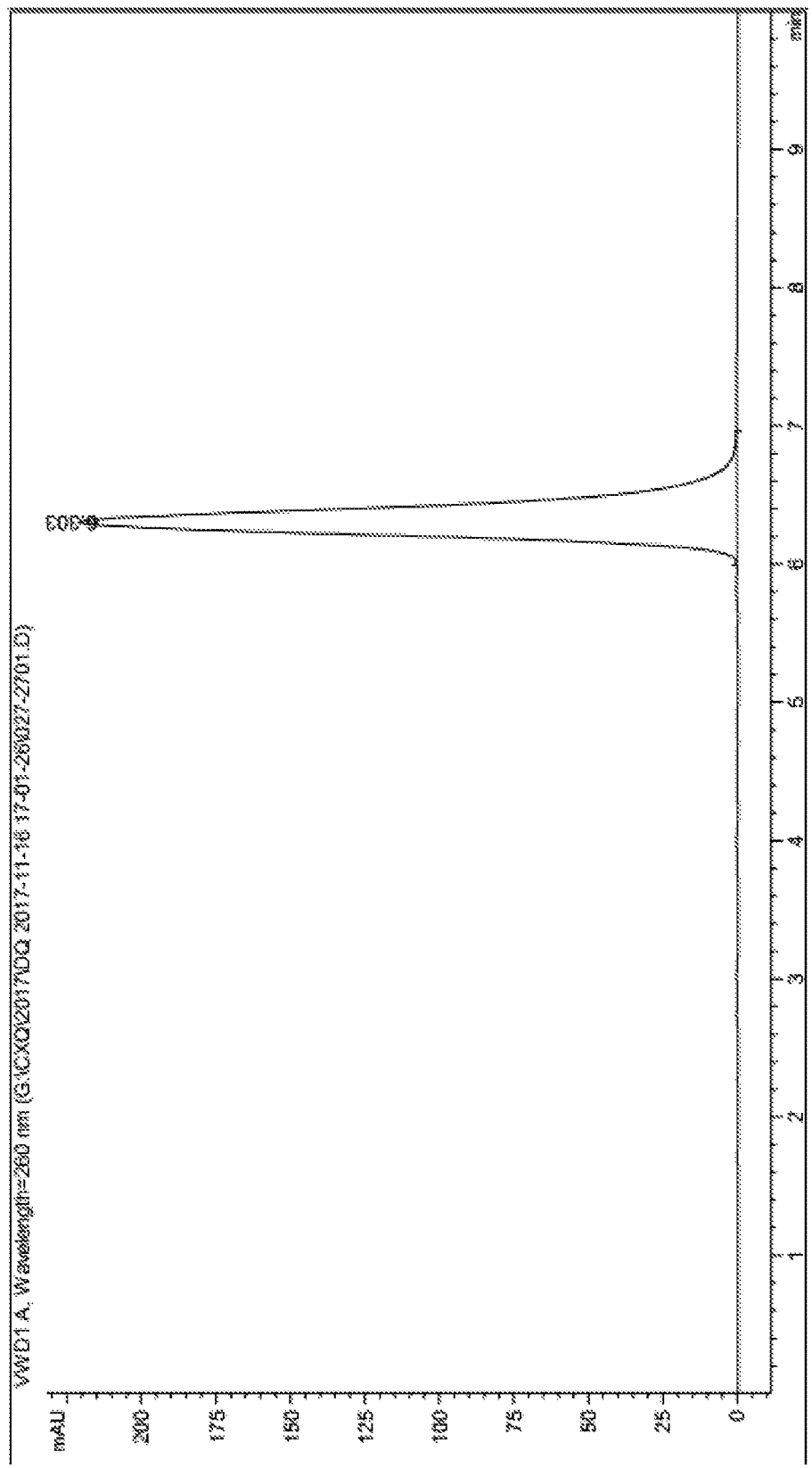
FIG. 17 shows that the solid solution prepared in Example 8 (F8) by the HME technique was treated with pH 9.0 solution for 10 days and the mixture was dialyzed, diluted and analyzed with the established HPLC method. The HPLC graph shows that decoquinate is not altered in either the peak pattern or the retention time of decoquinate in the HPLC analysis after the treatment with alkaline solution.

In general, a solid material can have crystal and non-crystal forms, and the temperature at which the crystal begins to melt is called the melting point (Tm). The melting point is the temperature at which a solid is converted from solid state to liquid state (melting). It can be generally expressed as Tm. Organic compounds generally have a fixed melting point, that is, under a certain pressure, changes between solid phase and liquid phase are very sensitive. The melting point range of a pure substance from solid to liquid is generally narrow. However, if the organic compound is mixed with other substances, the melting point will decrease, and the melting point range will widen. The melting point of decoquinate is 242 to 246° C. The present invention designs a specialized composition such that when decoquinate is mixed molten with excipients such as a hot-melt extrudable excipient, a plasticizer and the like, it can become a liquid state at a temperature significantly lower than its own melting point, which in turn reduces the possibility of its thermal decomposition (FIG. 14), and thus is in favor of retaining its original structure and pharmacological potency.

During the preparation of the solid solution of decoquinate of the present invention, the chemical structure of the active ingredient decoquinate remains unchanged so that its pharmacological activity is fully retained; in some examples, the extruded solid solution product of decoquinate is homogeneously suspended in the aqueous media and the suspension remains stable without appearing cloudy or having floating or precipitating material for at least one week; furthermore, the release or the dissolution rate of decoquinate formulated within the HME product of the present invention is significantly enhanced, and bioavailability and antimalarial effect in animal studies also significantly improved.

The present invention provides an application of the solid solution of decoquinate using the HME preparation method as a pharmaceutical formulation for prevention and/or treatment of a disease caused by *Plasmodium* parasites.

Preferably, said disease refers to one or more of the malarias caused by *Plasmodium vivax, Plasmodium falciparum, Plasmodium malariae, Plasmodium ovale*, and *Plasmodium knowlesi*.

The solid solution of decoquinate can be prepared into oral dosage forms such as tablets, granules, and filled capsules, if desired.

The hot-melt extrusion technique employed in the present invention can make an active pharmaceutical ingredient a solid solution, wherein decoquinate is melted and formulated within a hot-melt extrudable excipient, and thus the solid soluble decoquinate is formed and stabilized; in the present invention, excipients suitable for decoquinate solid solution and HME parameters appropriate for producing such solid solution are selected to optimize the condition and to generate the stable solid solution.

HPMCAS are produced by DOWs and have subtypes including 912, 716, and 126 in terms of substituted numbers of acetate or succinate group. Other manufacturers (Shin-Etsu, Japan & Ashland, UK) produce the identical products named L, M, and H accordingly. These cellulose based polymers are designed for spray drying techniques in formulating poorly soluble compounds and seem to have inconsistent physicochemical profiles in solubility enhancement and formulation stability when they are hot-melted with several compounds including itraconazole (slightly basic), ezetimibe (neutral), and felodipine (slightly acidic). The subtype of HPMCAS 126 or type H with the most abundant acetate substitution has been found to be better than the other two subtypes (HPMCAS 716 or 912 or Type L or M) for making decoquinate solid solution by the HME because it has the greatest effects on solubility enhancement and stability of formulation (Table 3). When suspended in aqueous media, it appears to be in homogeneous phase and glossy, and stable without precipitation and agglomeration for at least 24 hours. However, when two subtypes of HPMCAS were compared for decoquinate solid solution, one (AffiniSol™ 126) appeared to be superior to the other two (AffiniSol™ 912 and 716).

TABLE 3

Different subtypes of HPMCAS for decoquinate (DQ) solubility enhancement and formulation stability

| ShinEtsu & Ashland Product Type<br>Dow HPMC AS Equivalent | L<br>716 | M<br>912 | H<br>126 |
|---|---|---|---|
| Acetate (%) | 5.0-9.0 | 7.0-11.0 | 10.0-14.0 |
| Succinate (%) | 14.0-18.0 | 10.0-14.0 | 4.0-8.0 |
| Methoxyl (%) | 20.0-24.0 | 21.0-25.0 | 22.0-26.0 |
| Hydroxypropyl (%) | 5.0-9.0 | 5.0-9.0 | 6.0-10.0 |

TABLE 3-continued

Different subtypes of HPMCAS for decoquinate (DQ) solubility enhancement and formulation stability

| ShinEtsu & Ashland Product Type<br>Dow HPMC AS Equivalent | L<br>716 | M<br>912 | H<br>126 |
|---|---|---|---|
| Tg (° C.) | 119 | 120 | 122 |
| Solubility Enhancement | | >L | >M |
| Formulation Stability | | >L | >M |

Note:
HPMCAS = AFFINISOL™ Hypromellose Acetate Succinate
Tg ° C. = glass transition temperature The melted components of the compositions are extruded through a shape-forming outlet, and upon rapid cooling, remain a solid, single phase that is shelf-stable. At the same time, post extrusion processing equipment can be adapted to manage the extruded shape, making it amendable to downstream processing into a dosage form. In general, these extruded materials are milled to powder so that they can be incorporated into traditional oral solid dosage forms such as tablets or capsules, while maintaining the desired release profile for the drug.

Decoquinate in such a dispersion can be considered as a solid solution. To further improve the status of decoquinate in the dispersion when suspended in aqueous media, proper substances such as solubilizers or plasticizers are also added to the blend prior to HME process. Improved water solubility of decoquinate with nanoparticle size can enhance dissolution rate and help intestinal absorption and increases bioavailability and in vivo biological activity of the pharmaceutical drug. Thus, the improvement of decoquinate solubility is made by the stability of well dispersed status of the compound so that when suspended in aqueous media it remains to be in the media for at least 24 hours and may stay stable in aqueous phase for more than 12 months. In some examples of solid solution, without any further manipulations such as high-pressure homogenization and ultrasound disruption, nanoparticles in aqueous suspension of HME products are as small as 200 nm or ranging from 200 nm to 400 nm.

The present invention adopts the hot-melt extrusion technology to prepare the solid solution of decoquinate. The inventors select particular formulation excipients and a particular ratio of active component to the excipients so that when decoquinate is mixed molten with excipients such as polymeric carrier material, plasticizer and the like, it can become liquid at a temperature lower than its own melting point, which greatly reduces the possibility of its thermal decomposition, and is in favor of retaining its original structure and potency. Further, by optimizing the mechanical parameters, the active compound decoquinate and hot-melt extrudable excipients are efficiently melted, the extruded product is uniformly produced, and thereby the process according to the present invention is superior to organic solvent methods in enhancing oral bioavailability and potency of decoquinate; and compared with the related products prepared by the organic solvent method and the hot-melt method, the preparation process of the present invention is more likely to improve production efficiency, and thus making it easier to apply the laboratory achievements to the pilot scale up test and to the production level for marketing and further to the clinical application.

To facilitate understanding of the present invention, the embodiments of the present invention are described as follows. It should be understood by those skilled in the art that the examples are merely illustrative of the present invention and should not be regarded as the limitation of the invention thereto in any way.

The Materials Used in the Following Examples and their Sources

Decoquinate (batch number: 130802, molecular weight: 417.53; Zhejiang Genebest Pharmaceutical Co., Ltd.);

Propranolol standard (Sigma Chemical Co. (China branch));

Hydroxypropyl methylcellulose (AFFINISOL™ HPMC HME 15LV, HME 4M; Dow Pharma & Food Solutions, USA);

Hydroxypropyl methyl cellulose acetate succinate (AFFINISOL' HPMCAS-716, AS-912, and AS-126; Dow Pharma & Food Solutions, USA);

Dimethylaminoethyl methacrylate copolymer (EUDRAGIT®EPO, ROHM, EUDRAGIT, Germany);

Polyvinyl caprolactam—polyvinyl acetate—polyethylene glycol graft copolymer (Soluplus®, BASF, Germany);

Vinylpyrrolidone-vinyl acetate copolymers (Kollidon® VA 64, BASF, Germany); Poloxamer 188 (Kolliphor® P188 (BASF, Germany);

Polyethylene glycol glyceryl laurate (Gelucire® 44/14, GATTEFOSSE, France); Polyethylene glycol glyceryl stearate (Gelucire® 50/13 GATTEFOSSE, France); Polyoxyl 40 hydrogenated castor oil (Kolliphor® RH 40, BASF, Germany); Polyethylene glycols 6000 (PEG 6000, Sigma-Aldrich®, USA).

Example 1

In this example, a solid solution of decoquinate was prepared by using the HME method from a composition for HME comprising decoquinate as an active ingredient, Soluplus®, HPMC HME 15LV and PEG 6000. The decoquinate load is 10% of the total weight of the composition. The specific preparation procedure was as follows:

| | |
|---|---|
| Soluplus ® | 30 g |
| PEG 6000 | 20 g |
| HPMC HME 15LV | 130 g |
| Decoquinate | 20 g |

When the preset temperature values are reached, the blended was fed into the corotating twin screw extruder (Pharm 11) through the hopper and processed. The melting temperature of the twin-screw hot-melt extruder was set to 120-160° C. The screw speed was initially 50 rpm, and then depending on the pressure and torque figures on the machine display, if the figures were displayed within the normal range, the screw speed was turned up to 150 rpm. The feeding materials underwent heating at different segments of barrel, mixing, melting, and being pressed by extrusion, and then the melted materials extruded from the die in a stripped shape were instantly cooled to a solid at room temperature, which was then cut and pulverized.

Figure 4:
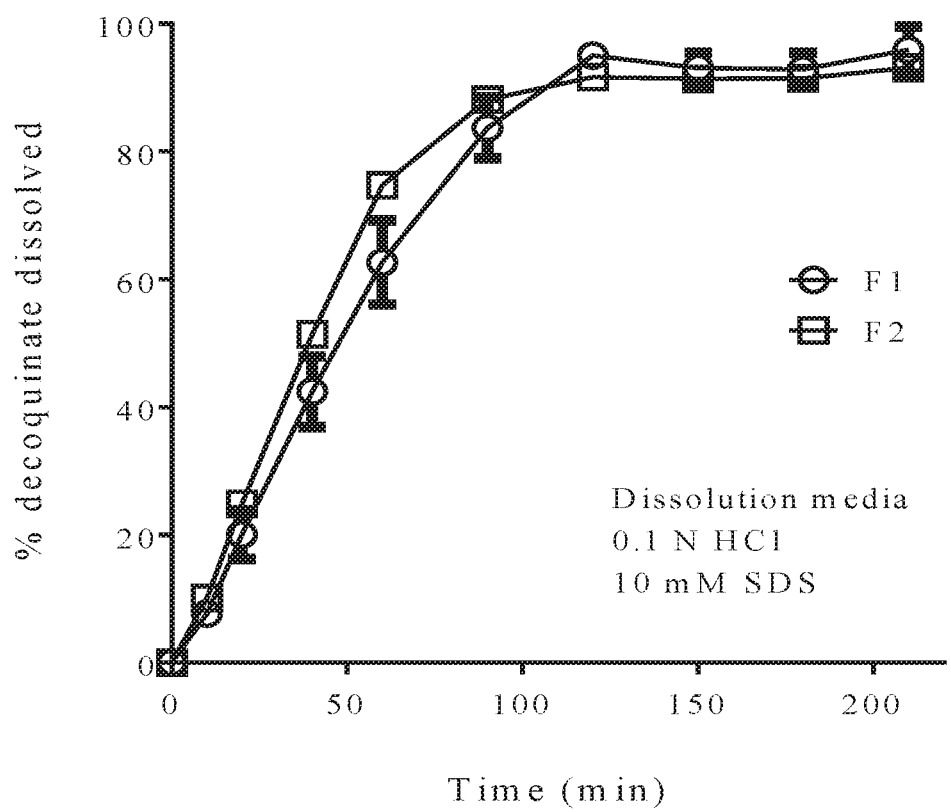
FIG. 4 illustrates a comparison of the in vitro dissolution rate of the solid solutions of decoquinate prepared in Example 1 and Example 2. The experiment was performed with dissolution media containing 0.1N HCl and 10 mM SDS as described in dissolution method. This dissolution media was generally used in all experiments unless it is indicated otherwise.

The product from this preparation appeared to be uniformed in PBS (pH 7.4) and was homogeneous when suspended in aqueous phase. The average particle size measured for the above suspended decoquinate was 1.01 µm; the cumulative dissolution percentage of decoquinate shown in FIG. 4.

Example 2

In this example, decoquinate product was prepared by the HME method from a composition for HME comprising decoquinate as an active ingredient, Soluplus®, HPMC HME 15LV and PEG 6000. The decoquinate load is 20% of the total weight of the composition. The specific preparation procedure was as follows:

| | |
|---|---|
| Soluplus ® | 27 g |
| PEG 6000 | 20 g |
| HPMC HME 15LV | 113 g |
| Decoquinate | 40 g |

The above weighed materials were fully mixed. The parameter settings for the hot-melt extruder and the operation procedures after feeding the blended material were the same as those of Example 1.

The extrudate appeared to be uniformed in PBS (pH 7.4) and was homogeneous when suspended in aqueous phase. The average particle size measured for the above suspended decoquinate was 1.097 µm; the cumulative dissolution percentage of decoquinate was shown in FIG. 4.

Example 3

The composition for HME comprised decoquinate, Soluplus®, HPMC HME 4M, and PEG 6000. The decoquinate load is 10% of the total weight of the composition. The specific preparation procedure was as follows:

| | |
|---|---|
| Soluplus ® | 30 g |
| PEG 6000 | 20 g |
| HPMC HME 4M | 130 g |
| Decoquinate | 20 g |

The above weighed materials were fully mixed. The parameter settings for the hot-melt extruder and the operation procedures after feeding the blended material were the same as those of Example 1 except that the melting temperature of the twin-screw hot-melt extruder was set to 120-180° C.

Figure 5:
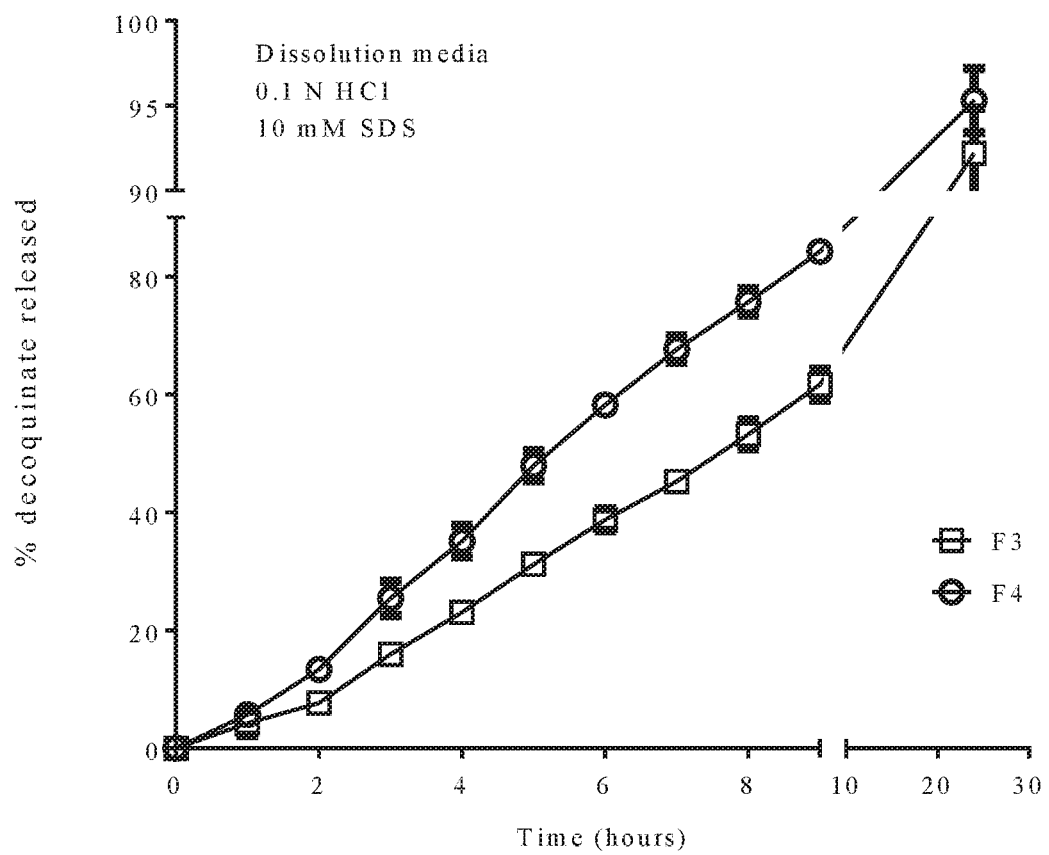
FIG. 5 illustrates a comparison of the in vitro dissolution rate of the solid solutions of decoquinate prepared in Example 3 and Example 4 by the HME technique under the dissolution condition as in FIG. 4.
Figure 6:
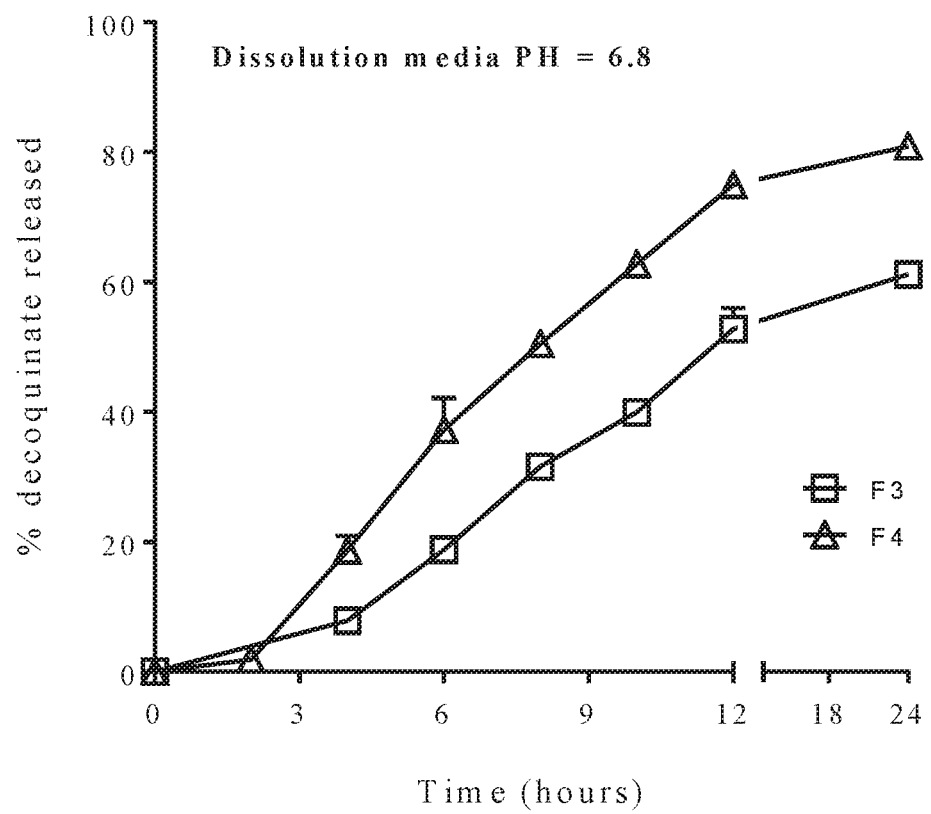
FIG. 6 illustrates a comparison of the in vitro dissolution rate of the solid solutions of decoquinate prepared in Example 3 and Example 4 by the HME technique using dissolution media of phosphate buffer with pH 6.8.

The extrudate appeared to be uniformed in PBS (pH 7.4) and was homogeneous when suspended in aqueous phase. The average particle size measured for the above suspended decoquinate was 4.385 µm; the cumulative dissolution percentage of decoquinate shown in FIGS. 5 and 6.

Example 4

The composition for HME comprised decoquinate, Soluplus®, HPMC HME 4M, and PEG 6000. The decoquinate load is 20% of the total weight of the composition. The specific preparation procedure was as follows:

| | |
|---|---|
| Soluplus ® | 27 g |
| PEG 6000 | 20 g |
| HPMC HME 4M | 113 g |
| Decoquinate | 40 g |

The above weighed materials were fully mixed. The parameter settings for the hot-melt extruder and the operation procedures after feeding the blended material were the same as those of Example 1 except that the melting temperature of the twin-screw hot-melt extruder was set to 120-180° C.

The extrudate appeared to be uniformed in PBS (pH 7.4) and was homogeneous when suspended in aqueous phase. The average particle size measured for the above suspended decoquinate was 2.232 μm; the cumulative dissolution percentage of decoquinate was shown in FIGS. 5 and 6.

Example 5

The composition for HME comprised decoquinate, HPMC HME 15LV, and Kolliphor® P188, RH 40. The decoquinate load is 20% of the total weight of the composition. The specific preparation procedure was as follows:

| | |
|---|---|
| HPMC HME 15LV | 90 g |
| Kolliphor ® P188 | 15 g |
| RH 40 | 15 g |
| Decoquinate | 30 g |

Figure 10:
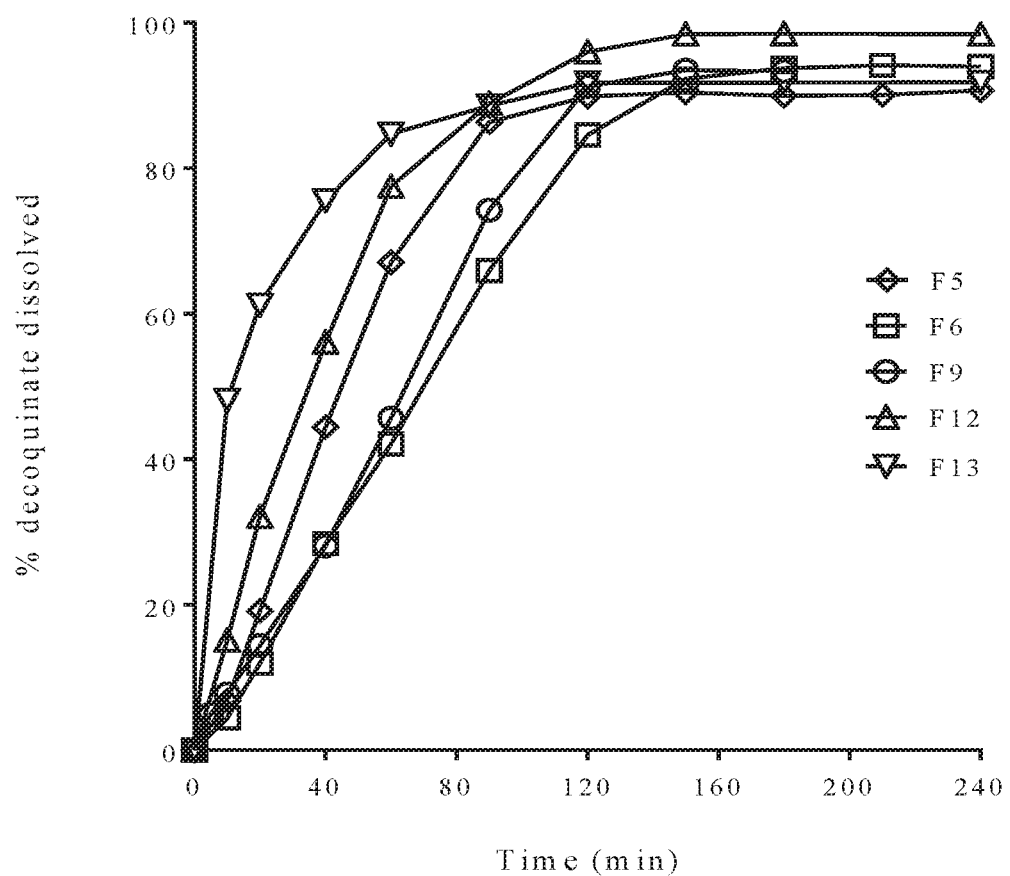
FIG. 10 illustrates a comparison of the in vitro dissolution rate of the solid solutions of decoquinate prepared in Example 5, Example 6, Example 9, Example 12, and Example 13 by the HME technique under the dissolution condition as in FIG. 4.

The above weighed materials were fully mixed. The parameter settings for the hot-melt extruder and the operation procedures after feeding the blended material were the same as those of Example 1. The extruded product appeared to be uniformed in PBS (pH 7.4) and was homogeneous when suspended in aqueous phase. The average particle size measured for the above suspended decoquinate was 898 nm; the cumulative dissolution percentage of decoquinate was shown in FIG. 10.

Example 6

The composition for HME comprised decoquinate, HPMC HME 15LV, and RH 40. The decoquinate load is 20% of the total weight of the composition. The specific preparation procedure was as follows:

| | |
|---|---|
| HPMC HME 15LV | 105 g |
| RH 40 | 15 g |
| Decoquinate | 30 g |

The above weighed materials were fully mixed. The parameter settings for the hot-melt extruder and the operation procedures after feeding the blended material were the same as those of Example 1.

The extruded product appeared to be uniformed in PBS (pH 7.4) and was homogeneous when suspended in aqueous phase. The average particle size measured for the above suspended decoquinate was 762 nm; the cumulative dissolution percentage of decoquinate was shown in FIG. 10.

Example 7

The composition for HME comprised decoquinate, Soluplus®, HPMCAS-912, and PEG 6000. The decoquinate load is 25% of the total weight of the composition. The specific preparation procedure was as follows:

| | |
|---|---|
| Soluplus ® | 28 g |
| PEG 6000 | 15 g |
| HPMCAS-912 | 70 g |
| Decoquinate | 37 g |

The above weighed materials were fully mixed. The parameter settings for the hot-melt extruder and the operation procedures after feeding the blended material were the same as those of Example 1.

Figure 7:
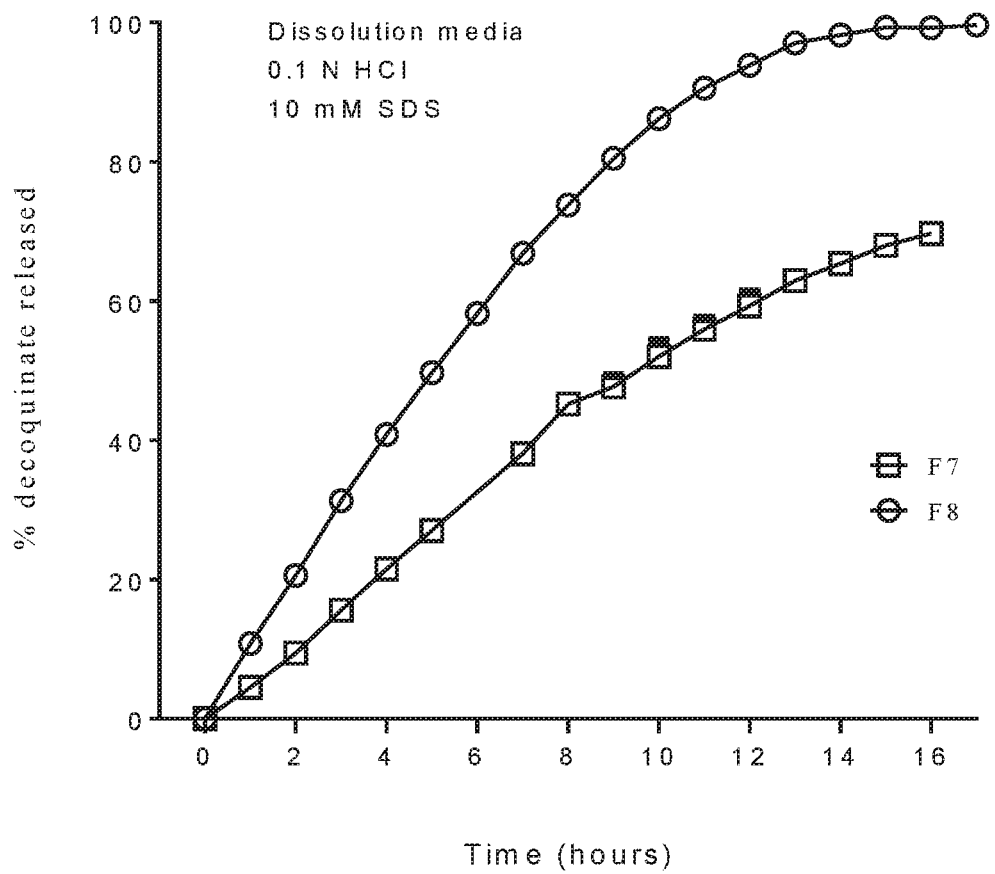
FIG. 7 illustrates a comparison of the in vitro dissolution rate of the solid solutions of decoquinate prepared in Example 7 and Example 8 by the HME technique under the dissolution condition as in FIG. 4
Figure 8:
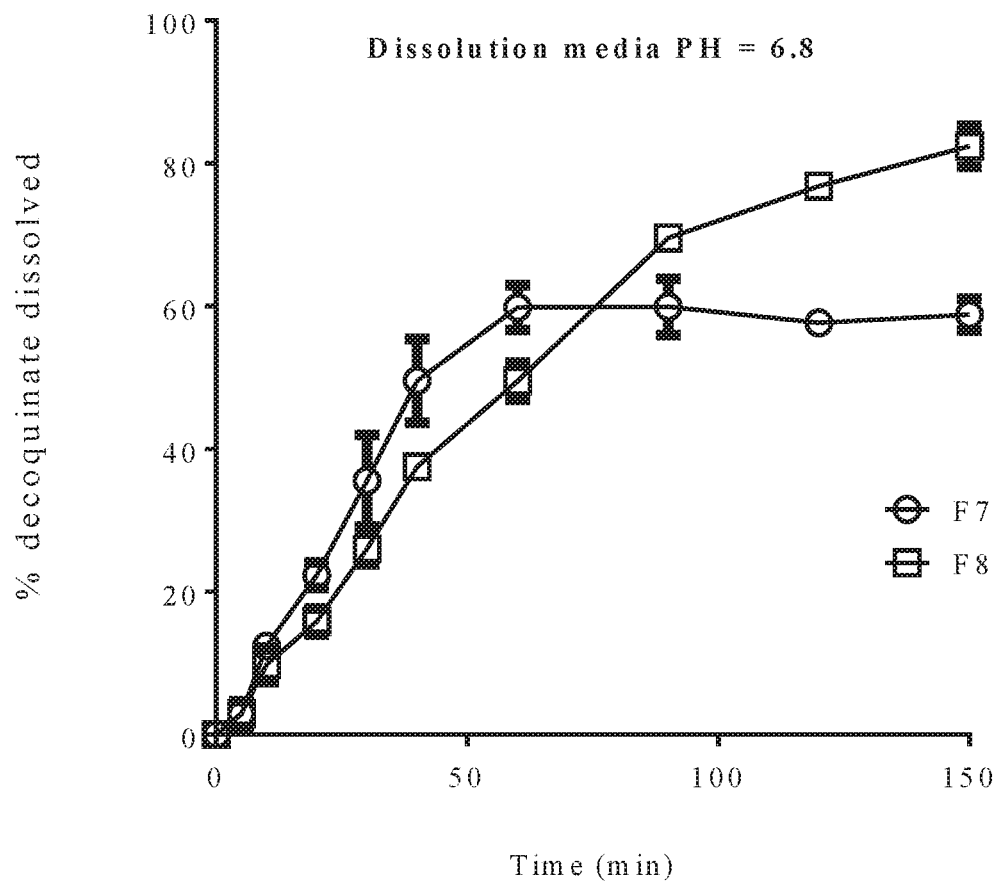
FIG. 8 illustrates a comparison of the in vitro dissolution rate of the solid solutions of decoquinate prepared in Example 7 and Example 8 by the HME technique using dissolution media of phosphate buffer with pH 6.8.

The product of decoquinate prepared in the present example was suspended in aqueous phase. The average particle size measured for the above suspended decoquinate was 588 nm; the cumulative dissolution percentage of decoquinate was shown in FIGS. 7 and 8.

Example 8

The composition for HME comprised decoquinate, Soluplus®, HPMCAS-126, and PEG 6000. The decoquinate load is 25% of the total weight of the composition. The specific preparation procedure was as follows:

| | |
|---|---|
| Soluplus ® | 28 g |
| PEG 6000 | 15 g |
| HPMCAS-126 | 70 g |
| Decoquinate | 37 g |

The above weighed materials were fully mixed. The parameter settings for the hot-melt extruder and the operation procedures after feeding the blended material were the same as those of Example 1.

The extruded product appeared to be uniformed in PBS (pH 7.4) and was homogeneous when suspended in aqueous phase. The solid solution of decoquinate prepared in the present example was suspended in aqueous phase and the suspension was stable with no precipitation or agglomeration after 24h. The average particle size measured for the above suspended decoquinate was 472 nm; the cumulative dissolution percentage of decoquinate was shown in FIGS. 7 and 8.

Example 9

The composition for HME comprised decoquinate, Soluplus®, Kollidon® VA 64 (vinylpyrrolidone vinylacetate copolymer), PGGS (Polyethylene glycol glyceryl stearate or Gelucire® 50/13), and P188 (Poloxamer 188 or Kolliphor® P188). The decoquinate load is 25% of the total weight of the composition. The specific preparation procedure was as follows:

| | |
|---|---|
| Soluplus ® | 25 g |
| Kollidon ® VA 64 | 105 g |
| PGGS | 14 g |
| P188 | 6 g |
| Decoquinate | 50 g |

The above weighed materials were fully mixed. The parameter settings for the hot-melt extruder and the operation procedures after feeding the blended material were the same as those of Example 1.

The extruded product appeared to be uniformed in PBS (pH 7.4) and was homogeneous when suspended in aqueous phase. The average particle size measured for the above suspended decoquinate was 820 nm; the cumulative dissolution percentage of decoquinate was shown in FIG. 10.

Example 10

The composition for HME comprised decoquinate, EPO (dimethylaminoethyl methacrylate copolymer or EUDRAGIT®EPO). The decoquinate load is 20% of the total weight of the composition. The specific preparation procedure was as follows:

| EPO | 120 g |
| Decoquinate | 30 g |

The above weighed materials were fully mixed. The parameter settings for the hot-melt extruder and the operation procedures after feeding the blended material were the same as those of Example 1.

Figure 9:
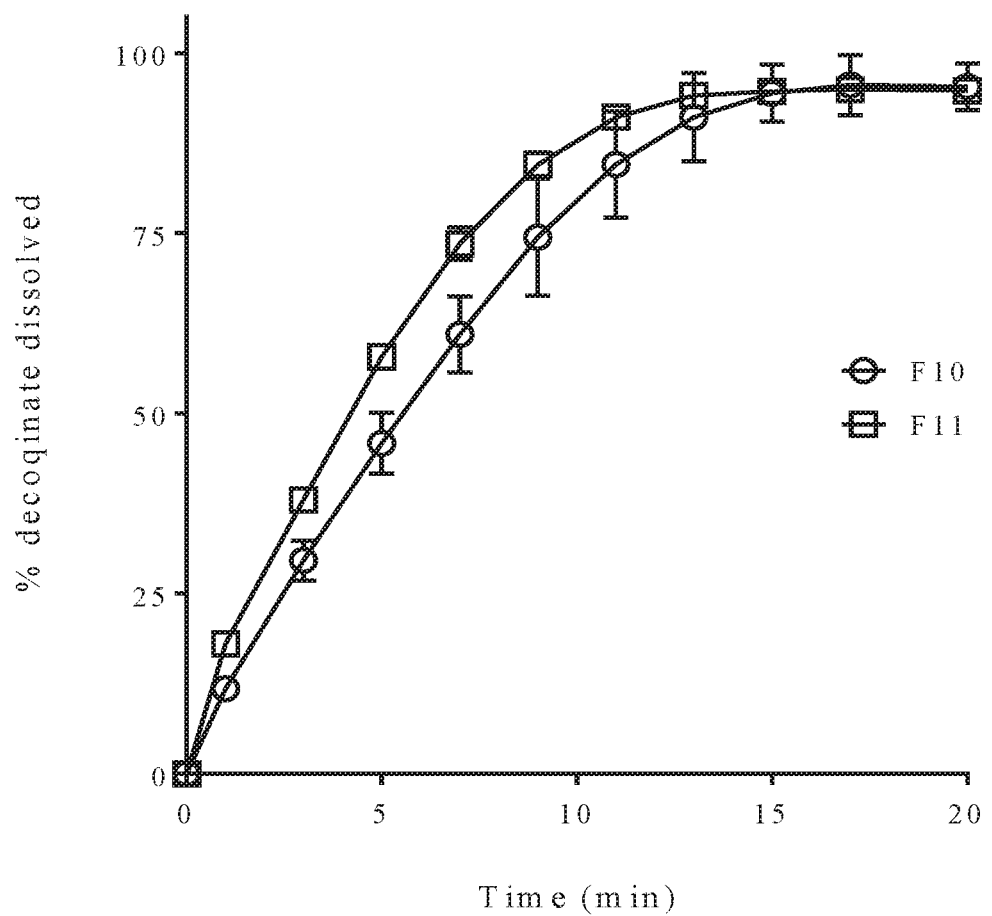
FIG. 9 illustrates a comparison of the in vitro dissolution rate of the solid solutions of decoquinate prepared in Example 9 and Example 10 by the HME technique under the dissolution condition as in FIG. 4.

The product from this preparation appeared to be uniformed in HCl (pH 4.0) and was homogeneous when suspended in aqueous phase. The average particle size measured for the above suspended decoquinate was 627 nm; the cumulative dissolution percentage of decoquinate was shown in FIG. 9.

Example 11

The composition for HME comprised decoquinate, Kollidon® VA 64 and EPO. The decoquinate load is 25% of the total weight of the composition. The specific preparation procedure was as follows:

| Kollidon ® VA 64 | 30 g |
| EPO | 120 g |
| Decoquinate | 50 g |

The above weighed materials were fully mixed. The parameter settings for the hot-melt extruder and the operation procedures after feeding the blended material were the same as those of Example 1.

The product from this preparation appeared to be uniformed in HCl (pH 4.0) and was homogeneous when suspended in aqueous phase. The average particle size measured for the above suspended decoquinate was 891 nm; the cumulative dissolution percentage of decoquinate was shown in FIG. 9.

Example 12

The composition for HME comprised decoquinate, Soluplus®, Kollidon® VA 64, and PEG 6000. The decoquinate load is 10% of the total weight of the composition. The specific preparation procedure was as follows:

| Soluplus ® | 30 g |
| Kollidon ® VA 64 | 130 g |
| PEG 6000 | 20 g |
| Decoquinate | 20 g |

The above weighed materials were fully mixed. The parameter settings for the hot-melt extruder and the operation procedures after feeding the blended material were the same as those of Example 1.

The product from this preparation appeared to be uniformed in saline solution (slightly acidic) and was homogeneous when suspended in aqueous phase. The average particle size measured for the above suspended decoquinate was 505 nm; the cumulative dissolution percentage of decoquinate was shown in FIG. 10.

Example 13

The composition for HME comprised decoquinate, Soluplus®, Kollidon® VA 64, and PEG 6000. The decoquinate load is 20% of the total weight of the composition. The specific preparation procedure was as follows:

| Soluplus ® | 27 g |
| Kollidon ® VA 64 | 113 g |
| PEG 6000 | 20 g |
| Decoquinate | 40 g |

The above weighed materials were fully mixed. The parameter settings for the hot-melt extruder and the operation procedures after feeding the blended material were the same as those of Example 1.

The extrudate appeared to be uniformed in saline solution (slightly acidic) and was homogeneous when suspended in aqueous phase. The average particle size measured for the above suspended decoquinate was 345 nm; the cumulative dissolution percentage of decoquinate was shown in FIG. 10.

Example 14

The composition for HME comprised decoquinate, Soluplus®, Kollidon® VA 64, and Gelucire® 50/13. The decoquinate load is 20% of the total weight of the composition. The specific preparation procedure was as follows:

| Soluplus ® | 74 g |
| Kollidon ® VA 64 | 37 g |
| Gelucire ® 50/13 | 10 g |
| Decoquinate | 30 g |

The above weighed materials were fully mixed. The parameter settings for the hot-melt extruder and the operation procedures after feeding the blended material were the same as those of Example 1.

Figure 11:
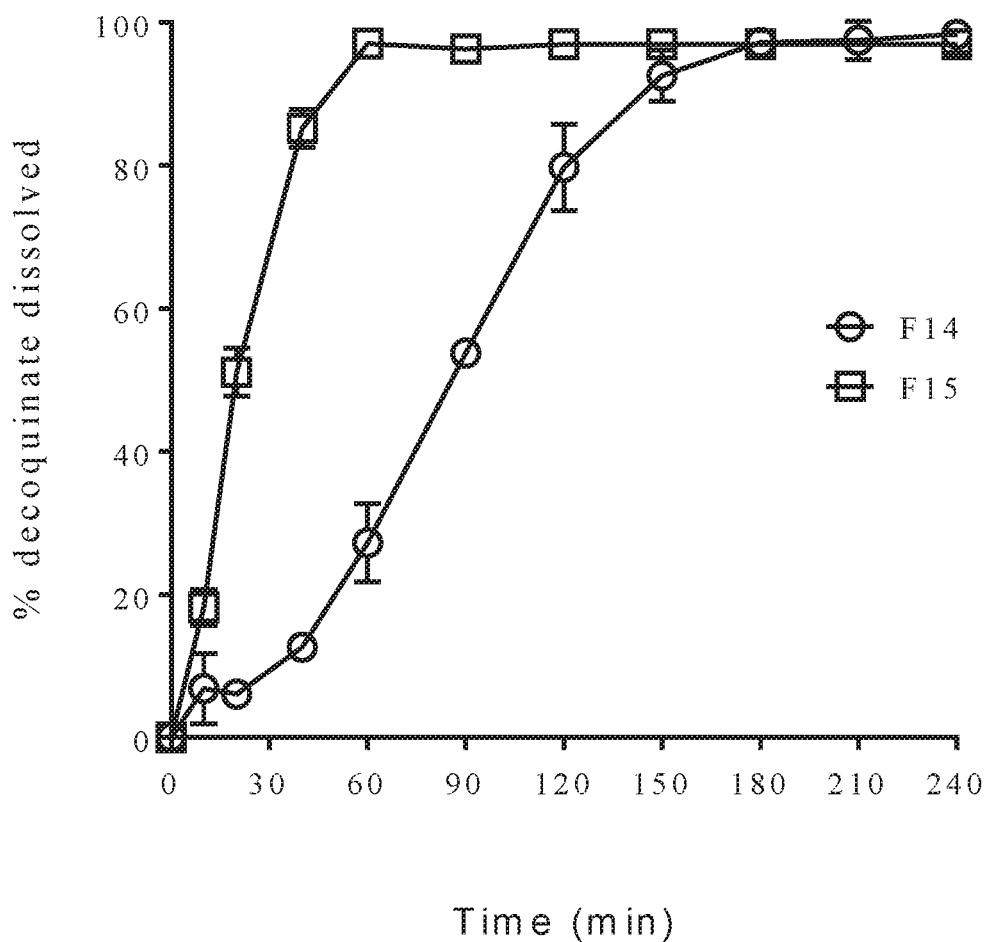
FIG. 11 illustrates a comparison of the in vitro dissolution rate of the solid solutions of decoquinate prepared in Example 14 and Example 15 by the HME technique under the dissolution condition as in FIG. 4.

The extrudate appeared to be uniformed in saline solution (slightly acidic) and was homogeneous when suspended in aqueous phase. The average particle size measured for the above suspended decoquinate was 317 nm; the cumulative dissolution percentage of decoquinate was shown in FIG. 11.

Example 15

The composition for HME comprised decoquinate, Soluplus®, Kollidon® VA 64, and PEG 6000. The decoquinate load is 25% of the total weight of the composition. The specific preparation procedure was as follows:

| Soluplus ® | 87 g |
| Kollidon ® VA 64 | 43 g |
| PEG 6000 | 20 g |
| Decoquinate | 50 g |

The above weighed materials were fully mixed. The parameter settings for the hot-melt extruder and the operation procedures after feeding the blended material were the same as those of Example 1.

The extrudate appeared to be uniformed in saline solution (slightly acidic) and was homogeneous when suspended in aqueous phase. The mean particle size of decoquinate prepared in the present example was small and stable in aqueous phase and the suspension had no precipitation or agglomeration 24h after stayed at room temperature. The average particle size measured for the above suspended decoquinate was 209 nm; the cumulative dissolution percentage of decoquinate was shown in FIG. 11.

Table 1 summarizes the percentage of each component in dry weight of decoquinate HME compositions from Example 1 to Example 8.

TABLE 1

| Formulation | Soluplus (g) | PEG6000 (g) | HPMC (g) | P188 (g) | RH 40 (g) | DQ (g) |
|---|---|---|---|---|---|---|
| 1 | 30 | 20 | 130 (15LV) | | | 20 |
| 2 | 27 | 20 | 113 (15LV) | | | 40 |
| 3 | 30 | 20 | 130 (4M) | | | 20 |
| 4 | 27 | 20 | 113 (4M) | | | 40 |
| 5 | | | 90 (15LV) | 15 | 15 | 30 |
| 6 | | | 105 (15LV) | | 15 | 30 |
| 7 | 28 | 15 | 70 (AS-912) | | | 37 |
| 8 | 28 | 15 | 70 (AS-126) | | | 37 |

Note:
Solupins ® = polyvinyl caprolactam-polyvinyl acetate-polyethylene glycol graft copolymer
PEG6000 = polyethylene glycol 6000;
HPMC = hydroxypropyl methylcellulose;
15LV = HPMC HME 15LV;
4M = HPMC HME 4M;
AS-912 = HPMCAS-912;
AS-126 = HPMCAS-126;
P188 = Poloxamer 188 (Kolliphor ® P188);
RH40 = polyoxyl 40 hydrogenated castor oil;
DQ = decoquinate Table 2 summarizes the percentage of each component in dry weight of decoquinate HME compositions from Example 9 to Example 15.

TABLE 2

| Formulation | Soluplus (g) | VA 64 (g) | Others (g) | DQ(g) |
|---|---|---|---|---|
| 9 | 25 | 105 | 14 (PGGS), 6 (P188) | 50 |
| 10 | | 120 | (EPO) | 30 |
| 11 | | 30 | 120 (EPO) | 50 |
| 12 | 30 | 130 | 20 (PEG6000) | 20 |
| 13 | 27 | 113 | 20 (PEG6000) | 40 |
| 14 | 74 | 37 | 10 (PGGS) | 30 |
| 15 | 87 | 43 | 20 (PEG6000) | 50 |

Note:
Soluplus ® = PEG 6000/vinylcaprolactam/vinylacetate copolymer
VA 64 = Vinylpyrrolidone/vinylacetate copolymer
PGGS = Polyethylene glycol glyceryl stearate (Gelucire ® 50/13)
P188 = Poloxamer 188 (Kolliphor ® P188)
RH40 = polyoxyl 40 hydrogenated castor oil
EPO = Dimethylaminoethyl methacrylate copolymer (EUDRAGIT ®EPO)
PEG 6000 = Polyethylene glycols 6000
DQ = decoquinate API in solution in the body is required for the absorption of the API and increase in its rate of dissolution improves the oral bioavailability of a poorly water-soluble API according to the Noyes-Whitney equation:

$$\frac{dW}{dt} = \frac{DA(C_s - C)}{L}$$

In the equation, dW/dt represents the dosage rate, A is the surface area of solid drug, Cs is the concentration of solid in the entire dissolution medium, C is the concentration of solid in diffusion surface that surrounds that solid; D is diffusion coefficient while L is the thickness of the diffusion layer. The larger the surface area of solid drug, the lower concentration of solid in diffusion surface and the thinner of the diffusion layer lead to the higher dosage rate. Solid solution has the features of fine particles distributed in homogeneous suspension which are thermodynamically stable and which favor the accelerated dosage rate.

The smaller particles dissolve faster and have higher solubility when released to the aqueous phase than the larger particles, as indicated in Ostwald-Freundlich equation.

$$\frac{RT}{M}\rho \ln\frac{S_1}{S_2} = 2\sigma\left(\frac{1}{r_1} - \frac{1}{r_2}\right)$$

In this equation, the solid drug that has smaller radius has higher solubility. A notable example of this relation is Ostwald ripening, in which surface tension causes small precipitates to dissolve and larger ones to grow. Normally after three months of storage at room temperature, Oswald ripening effect occurs in all substances. Cool temperatures delay the maturation of this effect, while higher temperatures accelerate the maturation. Some factors, such as lyophilization and spray-drying, affect particle agglomeration, particularly for the substances with large hydrophobic surfaces which harden during disaggregation and thus dissolution will be compromised after drying (Van Eerdenbrugh B, Froyen L, van Humbececk J, Mortens J A, Augustijns P, van den Mooter G. Drying of crystalline drug nanosuspensions—the importance of surface hydrophobicity on dissolution behavior upon redispersion. Eur J Pharm Sci, 2008; 35: 127-35.)

Figure 2:
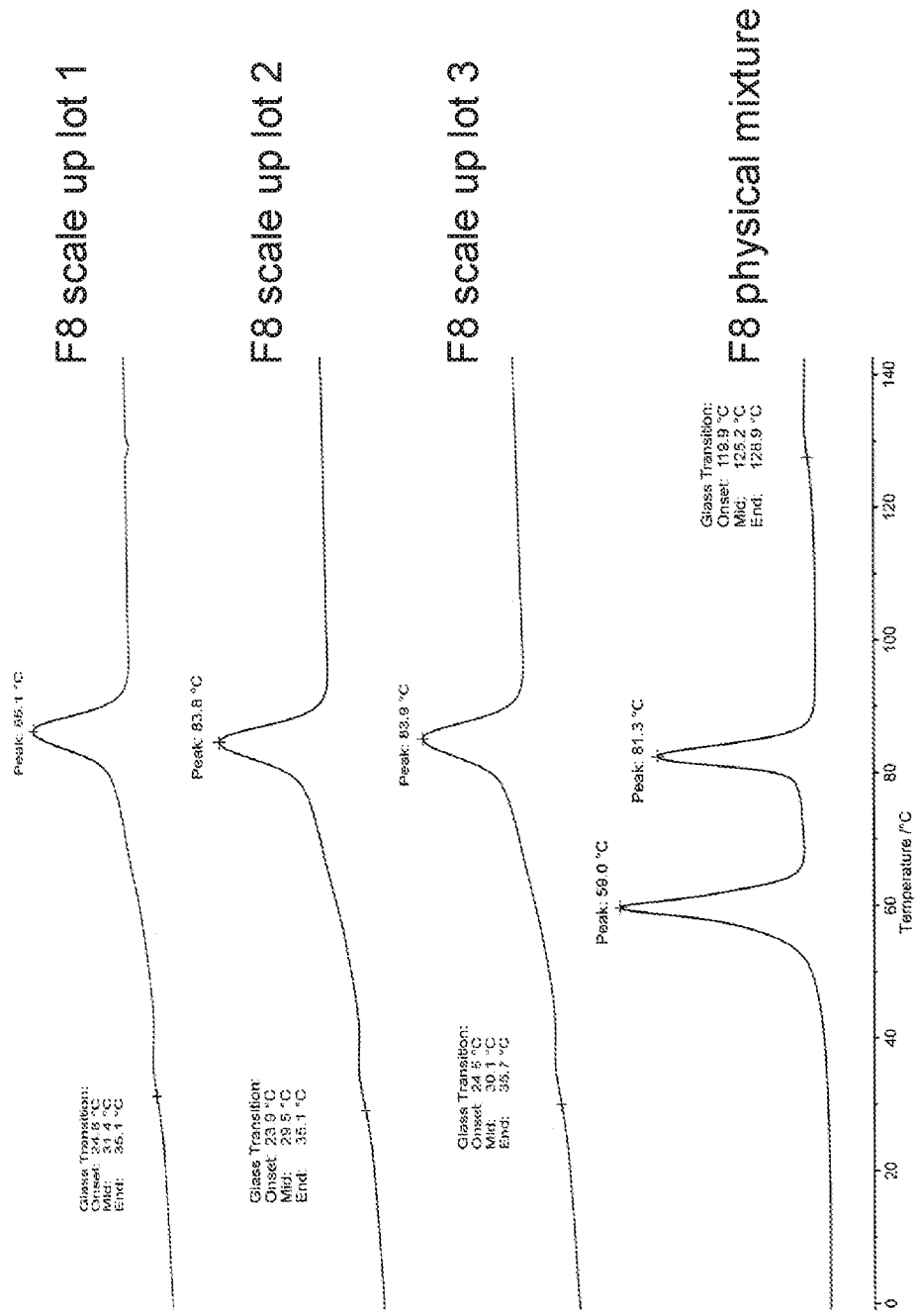
FIG. 2 is the graphs of Differential Scanning calorimetry (DSC) for hot-melt extrudate containing decoquinate as prepared in Example 8 (F8) but in three different lots of scale up preparation along with the DSC graph for physical mixture of decoquinate with the same excipients as in Example 8 (F8) at room temperature.
Figure 3:
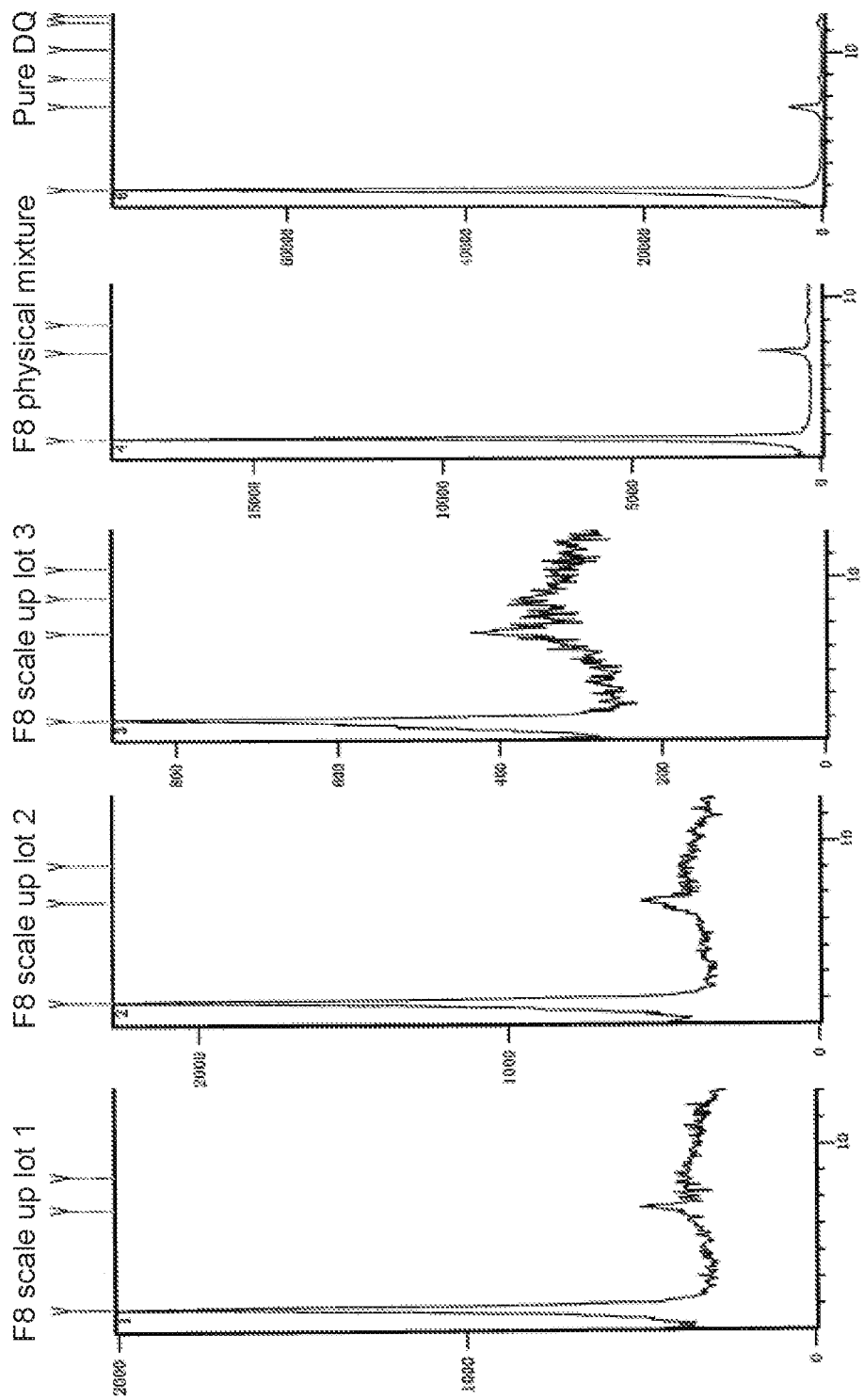
FIG. 3 is the analyses of X-ray diffractometer for the hot-melt extrudates. The samples are the same used for DSC in FIG. 2 (F8) besides the pure decoquinate shown in the last graph at right. Notice that the peaks shown in Y-axis with the scale up samples of three different lots are very small compared to the peaks of decoquinate in physical mixture (F8) and pure decoquinate.
Figure 13:
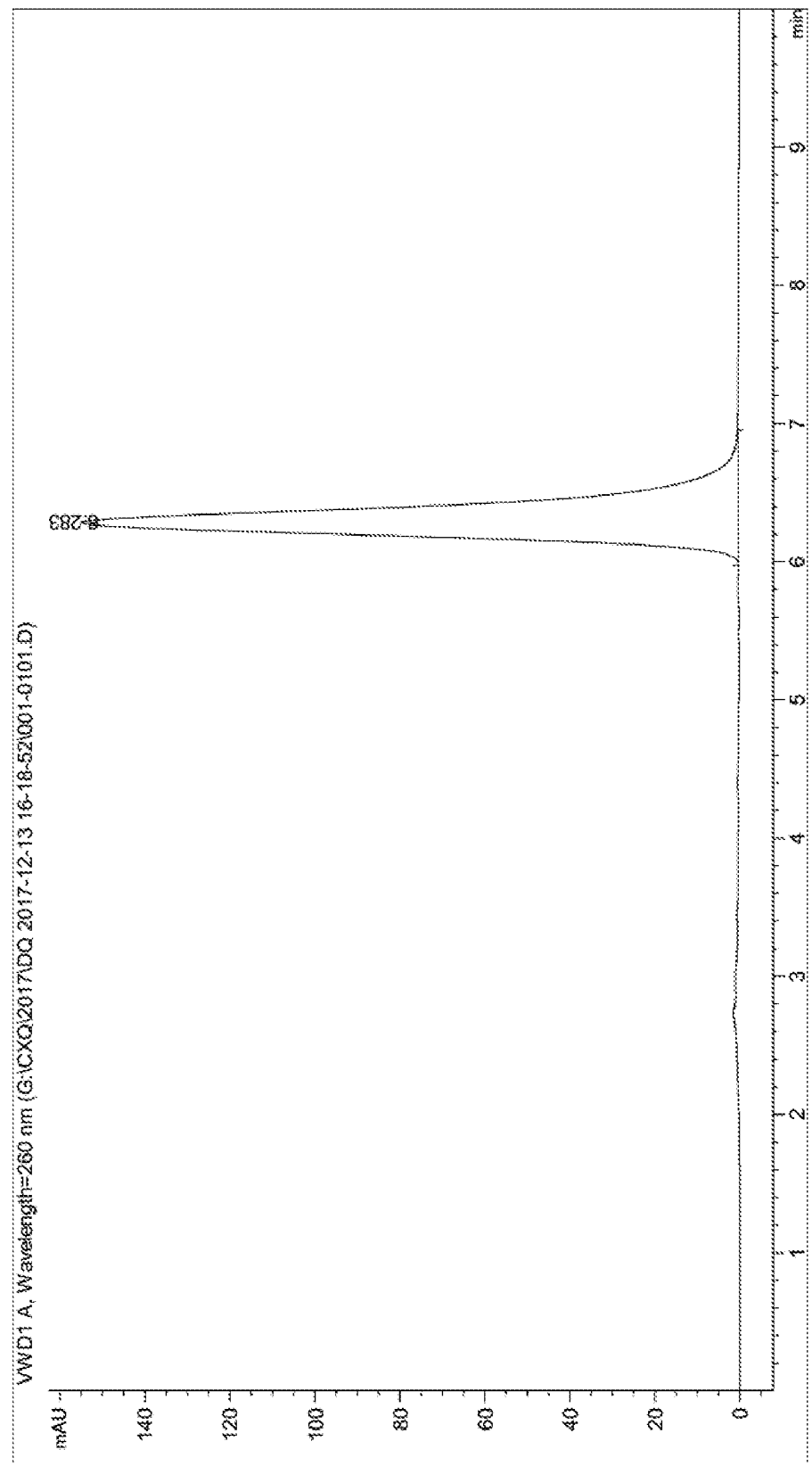
FIG. 13 is a HPLC analysis graph of decoquinate in HME compositions in Example 8 (F8); this figure shows that the decoquinate molecule is intact without change in either the peak pattern or the retention time of decoquinate in the HPLC analysis after preparation by the HME technique.

Thermogravimetric analysis showed that decoquinate molecules of solid solutions remained intact after the HME process (FIG. 1). Differential scanning calorimetry (DSC) analysis and X-ray diffraction analysis were performed for the selected formulations in the Examples described above. The data showed that decoquinate in the solid solution of all three large batches derived from the Example 8 (F8) had lost its original peak, indicating the fusion of API with the excipients through melting process compared to the decoquinate standard (FIGS. 2 and 3). High performance liquid chromatography (HPLC, Agilent 1260) analysis showed no change in retention time and the content of decoquinate in the products of all examples compared to the decoquinate standard, and after suspended in aqueous phase for 24 hours, decoquinate is above 90% of the drug load in all formulations except F11 (Table 4 and FIG. 13).

The particle size and zeta-potential of solid solutions of decoquinate were measured using a Dynamic Light Scattering (DLS) instrument, a particle size distribution analyzer (Zetasizer Nano ZSE, Malvern, UK). The HME output of each sample was suspended in water or PBS and sonicated (GT-2227QTS, Gute, Guangdong, China) for 2 min and about one ml was transferred to a cuvette supplied by the instrument manufacturer for the measurement. The Zetasizer system determines the size by measuring the Brownian motion of the particles in a sample using DLS and the particle size shown in Table 4 for each sample is a mean value for the size in intensity particle size distribution (PSD), which is considered as the standard report. Polydispersity index (PDI) is below 0.3 in all samples except F11 and F12 (Table 4).

Table 4 shows some physicochemical properties of decoquinate HME formulations from Example 1 to Example 15 (F1-F15). The amount of decoquinate in the aqueous phase determined by HPLC analysis is greater than 90% in 14 formulation samples after HME extrudates are suspended in the aqueous solutions as indicated and stand for at least 24 hours. To identify the particle size and polydispersity index (PDI) of decoquinate HME formulations 24 hours after suspended in aqueous phase, an aliquot of each sample was taken, diluted to the appropriate concentrations for measuring particle size. Except for F8, which was diluted with PBS (pH 7.4), all other samples were diluted with distilled water.

TABLE 4

| Examples | PS (nm) | PDI | Drug load A (%) | B (%) | B/A % | Solvents and pH |
|---|---|---|---|---|---|---|
| F1 | 1011 | 0.202 | 10 | 9.31 | 93.10 | PBS (pH 7.4) |
| F2 | 1097 | 0.055 | 20 | 19.44 | 97.20 | PBS (pH 7.4) |
| F3 | 4385 | 0.220 | 10 | 9.76 | 97.70 | PBS (pH 7.4) |
| F4 | 2232 | 0.185 | 20 | 19.62 | 98.10 | PBS (pH 7.4) |
| F5 | 898 | 0.255 | 20 | 18.94 | 94.70 | PBS (pH 7.4) |
| F6 | 762 | 0.204 | 20 | 18.74 | 93.70 | PBS (pH 7.4) |
| F7 | 588 | 0.235 | 25 | 23.43 | 93.72 | PBS (pH 7.4) |
| F8 | 472 | 0.180 | 25 | 24.73 | 98.90 | PBS (pH 7.4) |
| F9 | 820 | 0.233 | 25 | 24.83 | 99.32 | PBS (pH 7.4) |
| F10 | 627 | 0.238 | 25 | 24.55 | 98.20 | HCl (pH 4.0) |
| F11 | 891 | 0.343 | 25 | 21.10 | 84.40 | HCl (pH 4.0) |
| F12 | 505 | 0.352 | 10 | 9.57 | 95.70 | saline (~pH 5.5) |
| F13 | 345 | 0.184 | 20 | 18.25 | 91.25 | saline (~pH 5.5) |
| F14 | 317 | 0.235 | 20 | 18.72 | 93.60 | saline (~pH 5.5) |
| F15 | 209 | 0.154 | 25 | 24.13 | 96.52 | saline (~pH 5.5) |

Note:
PS = particle size;
PDI = polydispersity index
Drug load A (%) = designed percentage of decoquinate (API) in total dry weight composition
B (%) = actual measured percentage of decoquinate (API) in HME product of the total dry weight composition after suspended in aqueous media and standing for 24 hours at room temperature;
Solvents and pH: the HME products were milled into fine particle powder and suspended in the solution with pH as indicated for physicochemical characterization.

Thermogravimetric Analysis

The thermogravimetric analysis was done for a series of decoquinate HME samples and FIG. 2 shows the graph of thermogravimetric analysis of HME product made in Example 8 (F8). The amount of decoquinate was basically unchanged at a temperature below 250° C. and only began to decompose gradually at a temperature between 250° C. and 350° C. Any loss of the weight of decoquinate below 250° C. could be water molecules. Therefore, in all decoquinate HME products, the melting temperature used in the HME process was well below the one that could decompose decoquinate and therefore in the safe range.

Differential Scanning Calorimetry (DSC) Analysis

The hot-melt extruded products of decoquinate prepared in various examples were weighed and determined by DSC. Three preparations of Example 8 (F8) were made in a large scale which had API in kilogram per batch. FIG. 2 demonstrates the DSC analyses for three different scale up batches of Example 8 (F8) and the physical mixture of F8. The graphs indicate that the components of decoquinate HME products are fully intercalated with each other, which is quite different from the pattern for physical mixture of F8 which has each component remaining unchanged. The instruments used in the analysis included a balance with 0.0001 accuracy (Sartorius, available from Sartorius Scientific Instruments, model: BSA124S) and a differential scanning calorimeter (NETZSCH DSC 214 Polyma DSC21400A-0211-L, Germany).

The detection condition (N2: 40 mL/min) was set for the scanning procedure which was as follows. The temperature was increased from 20° C. to 150° C., stayed at this point for 5 min, then lowered the temperature to −20° C. at a rate of 20° C./min, stayed at −20° C. for 5 min, then raised the temperature from −20° C. to 150° C. again, recorded the second curve as the temperatures rose. The glass transition temperature (Tg) of each sample can be observed by the feature of curves as shown in FIG. 2.

The detection was carried out according to GB/T 19466.2-2004 plastic DSC (the second part): Determination of glass transition temperature. The hot melt extrudate containing decoquinate prepared in Example 8 (F8) had Tgs around 30° C. whereas the Tg of the physical mixture of decoquinate was around 125° C.

X-ray Diffraction Analysis

A ray diffractometer (Empyrean) was employed to perform analysis at the Test Center of Sun Yat-sen University in Guangzhou, China. The targeting material used is copper with CuKα radiation, and condition settings are voltage 40 kV, current 40 mA, divergence slits $\frac{1}{32}°$, anti-scatter slit $\frac{1}{16}°$, anti-scatter slit 7.5 mm, 2θ range: 3°-60°, step size 002°, time per step 40s. The graphs shown in FIG. 3 are the analyses of X-ray diffractometer for the hot-melt extrudates in Example 8 (F8) including the large preparations of three different lots, the pure decoquinate and physical mixture of Example 8 (F8). The peaks shown in Y-axis with the three decoquinate HME samples are very small compared to the peaks of decoquinate in physical mixture (F8) and pure decoquinate.

In Vitro Dissolution Test

The dissolution medium was a solution of 0.1N hydrochloric acid (HCl) and 10 mM sodium dodecyl sulfonate (SDS) unless indicated otherwise. The instrument used was RC-6 dissolution rate apparatus (Tianjin). The experiments were conducted by using the standard methods as described previously (PCT150162PPC). The amount of decoquinate dissolved in the media was determined by HPLC (Agilent, 1260). The mobile phase was an isocratic solution with 80% ethanol (0.1% formic acid) and 20% water (0.1% formic acid), and a wavelength 260 nm.

For Examples 3, 4, 7 and 8 (F3, F4, F7, F8), the drug dissolution tests were also done with phosphate buffer of pH 6.8.

Pharmacokinetic Experiments

An MS2 Turnover type oscillator from IKA Work's Guangzhou, China, and a 5415R high speed tabletop centrifuge from Eppendorf AG, Germany were used for sample treatment. Chromatographic analyses were performed with a HPLC system consisting of a LC-10ADvp Pump (SHIMADZU, Japan), MPS3C automatic sampler (Gerstel Auto sampler, Germany) and API3000 triple quadrupole tandem mass spectrometer (AB co., U.S.). All chemicals and solvents were of analytical grade. Water was purified using a Millipore (AK, USA) laboratory ultra-pure water system (0.2 μm filter).

A standard curve was prepared by dissolving decoquinate 50 μg/ml in ethanol which was diluted with ethanol to eight gradient concentrations ranging from 0.5 ng/ml to 500 ng/ml. Twenty microliters (20 μl) of each concentration solution and 100 μl blank blood were added to 1.5 ml tubes and mixed.

After vortexing for 3 minutes (Scilogex, US), 400 μl ethanol/acetonitrile (1:1) containing internal standard (propranolol 1000 ng/ml) were added to the tubes and mixed by vortex for another 5 min. The tubes were centrifuged at 16000 g for 60 min at 4° C. Subsequently, 100 μl of the supernatant was placed into the 96 well plate and analyzed by an LC/MS/MS System (Applied Biosystems-Sciex model for API 3000 mass spectrometer). For measuring drug concentrations in animal blood samples, the same procedures were carried out using 100 μl sample blood instead of blank blood. The samples for quality control were at three different levels representing low, middle and high concentrations of decoquinate. The chromatographic column was Agilent ZORBAX Eclipse Plus C8 (2.1×50 mm, 3.5-Micron). The mobile phase consisted of 0.1% formic acid in methanol: 0.1% formic acid in water (90:10: v/v) at a flow rate of 600 µl/min. The column temperature was 30° C. and the temperature of injector was 15° C.

Figure 12:
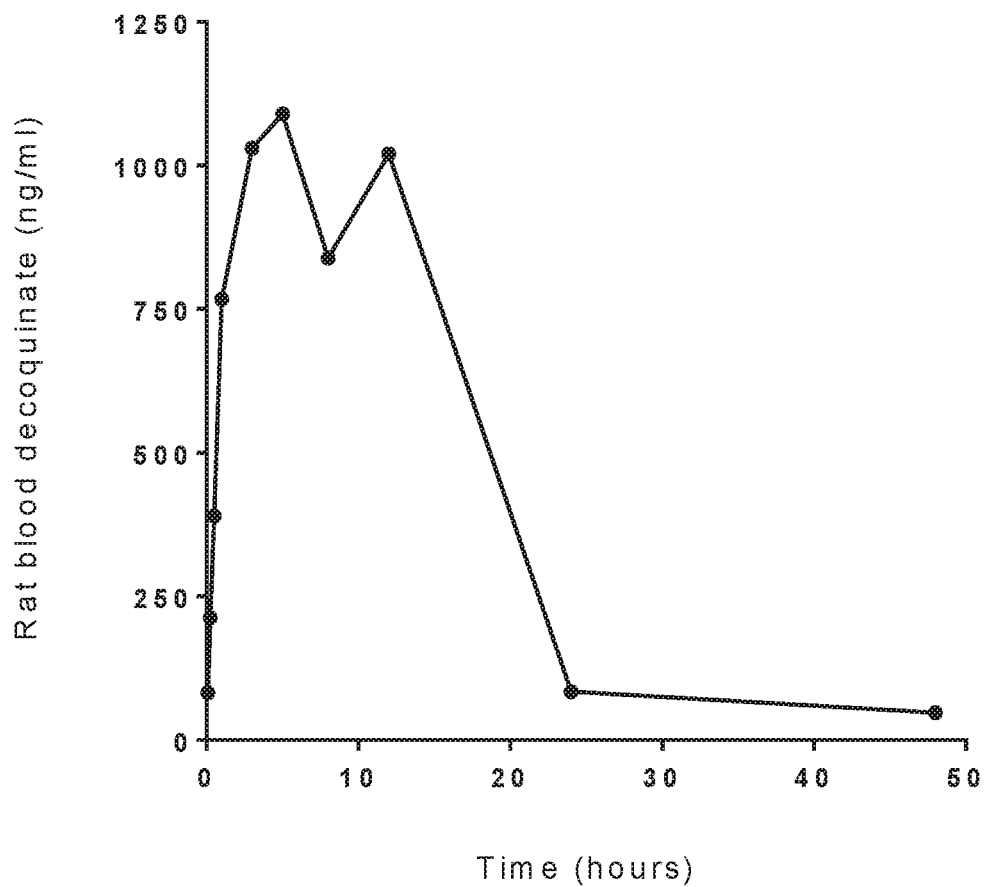
FIG. 12 illustrates a pharmacokinetic study of Example 8 (F8) performed in Sprague Dawley rats; F8 HME nanoparticle formulation was given to Sprague Dawley rats in a group of 4 by intragastric administration and decoquinate concentration in the plasma was measured by LC/MS. The ordinate represents the concentration of decoquinate in the blood and the abscissa represents the collection timing of animal blood samples.

Sprague-Dawley male rats (200-250 g, from Southern Medical University, China) were used to evaluate the HME formulations of decoquinate in the pharmacokinetic studies. All rats were weighed and administrated at a dose of 20 mg/kg of decoquinate. The solid solution of decoquinate was suspended in sterile saline solution with decoquinate 2 mg/ml and administered by intragastric gavage. After a single dosing, 200 µl of whole blood was withdrawn from the tail vein at 5, 15, 30 minutes, and 1, 3, 5, 8, 12, 24 and 48 hours (FIG. 12). The samples were collected with tubes containing heparin. Blood samples were treated by protein precipitation method. The mixture of ethanol and acetonitrile (1:1) was used as protein precipitation reagent. For protein precipitation, 20 µl ethanol and 100 µl blood samples were added to 1.5 ml tube and vortexed for 3 min, then 400 µl precipitation solution (ethanol acetonitrile) containing internal standard was added and vortexed for 5 min. Upon storage and standing still at room temperature for 8h, the samples were then vortexed for 5 min, and then centrifuged at 16000 g for 60 min at 4° C. The active substance was extracted from the samples and analyzed by the same procedures as described for the method of setting up the standard curve of decoquinate for LC/MS/MS System.

FIG. 12 is a graph showing the pharmacokinetic profiles of Example 8 (F8), wherein the ordinate indicates the concentration of decoquinate in the blood and the abscissa indicates the animal blood sampling time.

In Vitro Antimalaria Activity of Decoquinate Solid Solutions

Fifteen different preparations of decoquinate solid solutions as described in Examples were tested in cell culture assays to assess the growth inhibition of blood stage *Plasmodium* in freshly isolated human blood cells and the growth inhibition of *Plasmodium* in the liver stage in cell culture of HepG2 cells. The malaria SYBR fluorescence (MSF) assay was performed to detect the parasite DNA of *Plasmodium falciparum* in late-ring or early-trophozoite stages. Human *P. falciparum* strains in 0.5% parasitemia and 2% hematocrit were co-cultured with different concentrations of test compound in 96-well plates for 72h with 5% CO2 at 37° C. before ending the culture by adding lysis buffer containing SYBR Green I dye to each well and measuring growth inhibition of *P. falciparum* in host human erythrocytes. The intensity of fluorescence generated by the binding of SYBR Green I dye to *Plasmodium* DNA is quantitatively proportional to the number of parasites. The detailed description of method refers to SOP of the inventors.

For the inhibition of liver stage development assay (ILSDA), HepG2 liver cells were cultured with *Plasmodium berghei* sporozoite expressing firefly luciferase in the presence of a series of dilutions of test compound. In the case of formulations, the compound concentration was determined by the quantitation of HPLC. This assay is a modification of the method previously described by Ploemen et al. (PLoS One 2009, 4: e7881). The culture was maintained in microtiter plates for 48 hours after sporozoite invasion and intracellular proliferation of *P. berghei* parasites in HepG2 cells. The growth inhibition of the parasites by the test compound or the compound complexed with the excipients was determined by measuring the luminescent intensity produced by the process of luciferase catalyzing the substrates which were added by the end of incubation.

Table 5 shows the inhibitory effects of decoquinate on the liver stage of *Plasmodium berghei* ANKA 868 expressing luciferase. The experiments were carried out on HepG2 cells incubated with the sporozoites isolated from salivary glands of infected mosquitoes. The formulations tested were F8 and F15 prepared as described in Example 8 and Example 15. The concentration of decoquinate in the formulation composition used in the experiments was determined by HPLC measurements. The F8 and F15 were made in aqueous suspension and tested for inhibiting *Plasmodium* activity at days 64, 70, and 79 after the suspensions were made and stored at 4° C. The results were expressed by the half maximal inhibition concentration (IC50).

TABLE 5

The inhibitory effects of decoquinate in HME formulation (F8 and F15) on *Plasmodium berghei* ANKA 868 expressing luciferase at the liver stage.

| | F8 (IC50 (nM)) | | F15 (IC50 (nM)) | | PQ | |
|---|---|---|---|---|---|---|
| Period post prepration | Mean (n = 3) | SD | Mean (n = 3) | SD | Mean (n = 2) | SD |
| Day 64 | 0.43 | 0.03 | 0.40 | 0.01 | 1732.00 | |
| Day 70 | 0.31 | 0.06 | 0.30 | 0.02 | | |
| Day 79 | 0.17 | 0.06 | 0.18 | 0.02 | | |

Table 6 is the results showing in vitro antimalarial potency of decoquinate HME formulations prepared from Example 8 (F8) and Example 15 (F15). The inhibitory effects of decoquinate on different species and on different sources of *Plasmodium falciparum* at the blood stage were demonstrated by the half maximal inhibition concentration (IC50). Chloroquine and artemisinin were used as positive controls in the same experiments.

TABLE 6

The inhibitory effects of decoquinate solid solutions on some species of *Plasmodium falciparum* at the blood stage and the potency expressed as the half maximal inhibition concentration (IC50).

| Formulations/drugs | F8 | | | F15 | | | Chloroquine | | | Artemisinin | | |
|---|---|---|---|---|---|---|---|---|---|---|---|---|
| IC50 (nM) | Mean | n | SD | Mean | n | SD | Mean | n | SD | Mean | n | SD |
| Pf3D7 | 2.09 | 5 | 0.69 | 2.51 | 5 | 0.54 | 57.45 | 3 | 0.13 | 23.12 | 3 | 0.81 |
| pfDd2 | 3.41 | 3 | 0.29 | 2.53 | 5 | 0.82 | 243.90 | 3 | 6.08 | 26.01 | 3 | 0.85 |
| Pf803 | 2.65 | 8 | 0.42 | | | | 957.20 | 3 | 132.20 | 32.00 | 3 | 0.85 |
| pfB74F6 (PS) | 2.33 | 3 | 0.75 | | | | 79.20 | 3 | 4.45 | 14.47 | 3 | 3.57 |

TABLE 6-continued

The inhibitory effects of decoquinate solid solutions on some species of *Plasmodium falciparum* at the blood stage and the potency expressed as the half maximal inhibition concentration (IC50).

| Formulations/drugs | F8 | | | F15 | | | Chloroquine | | | Artemisinin | | |
|---|---|---|---|---|---|---|---|---|---|---|---|---|
| IC50 (nM) | Mean | n | SD | Mean | n | SD | Mean | n | SD | Mean | n | SD |
| pfB47D6 (PS) | 2.68 | 3 | 0.79 | | | | 78.15 | 3 | 7.03 | 25.44 | 3 | 1.77 |
| pfB64G11 (PS) | 2.21 | 3 | 0.48 | | | | 30.38 | 3 | 0.14 | 6.66 | 3 | 1.54 |
| pfB74C4 (PS) | 4.07 | 4 | 0.98 | | | | 59.29 | 3 | 0.74 | 26.41 | 3 | 0.60 |
| pfB12D9 (PS) | 3.47 | 4 | 0.61 | | | | 63.30 | 3 | 4.03 | 24.12 | 3 | 1.80 |

Note:
Pf: *Plasmodium falciparum*;
PfDd2: multidrug resistance species including chloroquine;
Pf803: chloroquine resistance *Plasmodium*;
PS: samples collected from patients Table 7 demonstrates the stability of decoquinate HME formulation produced in 3 large scale (kilogram) preparations from Example 8 (F8). The HME solid solutions were treated with alkaline buffer (pH 9), or with high temperature (60° C.) or with high humidity (92%) for 5 or 10 days respectively and then used for testing decoquinate inhibitory effects in in vitro blood stage experiments using freshly prepared red blood cells infected with *Plasmodium* Pf803 or PfB12D9. The base pH was neutralized by dialysis of decoquinate HME samples before used in cell culture experiments.

TABLE 7

The examination of the stability of F8 solid solution by measuring the inhibition potency against 2 species of *Plasmodium falciparum*

| P. falciparum | Pf803 | | | PfB12D9 | | |
|---|---|---|---|---|---|---|
| IC50 (nM) | Mean | n | SD | Mean | n | SD |
| F8 | 3.00 | 8 | 0.42 | 3.47 | 4 | 0.61 |
| F8 LB1 | 2.65 | 3 | 0.59 | 4.25 | 3 | 0.79 |
| F8 LB2 (SB) | | | | 3.50 | 3 | 0.77 |
| F8 LB2 (HH1) | | | | 3.43 | 3 | 0.50 |
| F8 LB2 (HH2) | 2.29 | 3 | 0.60 | | | |
| F8 LB2 (HT1) | 2.65 | 3 | 0.18 | | | |
| F8 LB2 (HT2) | 2.91 | 3 | 0.25 | | | |
| F8 LB3 | 3.45 | 3 | 0.03 | | | |

Note:
F8 is the HME solid solution prepared in Example 8
LB: F8 prepared in Example 8 in large batches (API kg per batch)
SB: strong base (pH 9) treated F8 solid solution
HH1: F8 treated in high humidity (92%) for 5 days
HH2: F8 treated in high humidity (92%) for 10 days
HT1: F8 treated in high temperature (60° C.) for 5 days
HT1: F8 treated in high temperature (60° C.) for 10 days In Vivo Efficacy Experiment The NIH-Swiss female mice used for the experiment were raised for at least 7 days after arrival. At the start of the experiment, the mice were 7 weeks old. Only one mouse was housed in each cage and maintained in a room with a temperature range of 18 to 26° C. with a relative humidity of 34% to 68% in a 12/12h light-dark cycle. Food and water were provided ad libitum during quarantine and throughout the study. This experiment was carried out in strict accordance with the relevant animal testing regulations (the Chinese State Council's Laboratory Animal Management Regulations, Revised Mar. 1, 2017). The decoquinate suspension used in the animal experiment was from the product of Examples 2, 8, 9, 11, 12 and 15 (F2, F8, F9, F11, F12 and F15), prepared with saline and subjected to ultrasonic treatment for 5 minutes. Each animal experiment was repeated at least three times with a group of 5 each time, so that at least 15 mice were tested in each group. The mice were inoculated with *Plasmodium* parasites by an injection of 50,000 sporozoites of *Plasmodium berghei* ANKA (Pb 868 sporozoites) through the tail vein of each mouse. Testing compound or formulation compound was administered to mice by PO (oral administration, by the manually intragastric method) the day before, the day of, and the next day after *Plasmodium* inoculation. The formulation compound suspended in saline were quantitated by HPLC method before dosing animals. The positive control was primaquine, an antimalarial drug used for the liver-stage *Plasmodium*. The vehicle control was the components used in the solid dispersion of decoquinate other than decoquinate. No anti-malarial activity was found with the vehicle control, the results of which were consistent with those obtained by using only saline as a negative control. The detection of *Plasmodium* parasitemia was performed as follows: a conventional method was used to count red blood cells per $mm^3$ of blood in that a thin film of blood was prepared and stained with 3% Giemsa for 20 minutes; and then the number of infected red blood cells per 1000 red blood cells was counted under oil microscope to obtain erythrocyte infected rate (EIR, ‰). If the parasites were not seen in the thin film, the thick film was prepared for detection of parasites and the results expressed as the parasite number per 100 white blood cells (WBC). Survival rates were calculated on day 60 post-infection for the still live mice versus the dead mice.

Table 8 shows the efficacy of the product prepared in the examples listed against *Plasmodium berghei* ANKA infection in NIH-Swiss female mice. The dosage of all HME products of decoquinate tested was at decoquinate 5 mg/kg body weight, the negative control group used was saline, and the positive control group used 30 mg primaquine per kg body weight. The results shown were the number of infected mice on day 12 from the microscopic detection of parasites of thin or thick films. The results also include the protection rate on day 12 and survival rate on day 60. The products from F8, F9, F11 and F15 have 100% survival rates whereas PQ, F2 and F12 have survival rates of 80%. These results demonstrate that the antimalarial activity of the composition from hot-melt extrudates can effectively prevent the mice from the infection of *Plasmodium* sporozoites in contrast to the zero protection and zero survival rate in saline control group.

Table 8 illustrates efficacy studies of the HME compositions prepared in various examples in mice infected with *Plasmodium berghei* expressing luciferase; wherein decoquinate given to animals at a dose of 5 mg per kg was in the saline suspension of F2, F8, F9, F11, F12, and F13 HME preparations; the saline group as a negative control; PQ represents the primaquine group used as a positive control at a dose of 30 mg per kg body weight. The animals were dosed by intragastric administration the day before, the same day, and the day after the parasite sporozoites (each mouse injected 50,000 sporozoites) were given by intravenous injection. *Plasmodium* infection in animals was examined under microscopic visualization of parasites in thin smears or thick smears prepared by taking a drop of blood from an individual mouse followed by Giemsa staining. Protection rates were calculated according to the data of parasitemia detection in mice on day 12 of *Plasmodium* sporozoite inoculation and the survival rates in each group on day 60 post the sporozoite inoculation.

TABLE 8

The causal prophylactic activities of decoquinate prepared in the form of solid solutions following daily intragastric administrations against sporozoite inoculation of the ANKA strain of *P. berghei* intravenously in female NIH-Swiss mice

| Formulations & drugs | Dose (mg/kg) | N in a group | Day 12 Infected | Protected rate | Day 32 Survived | Survival rate |
|---|---|---|---|---|---|---|
| Saline | 0 | 5 | 5 | 0 | 0 | 0 |
| PQ | 20 | 5 | 2 | 60 | 4 | 80 |
| F2 (DQ) | 5 | 5 | 2 | 60 | 4 | 80 |
| F8 (DQ) | 5 | 5 | 3 | 40 | 5 | 100 |
| F9 (DQ) | 5 | 5 | 2 | 60 | 5 | 100 |
| F11 (DQ) | 5 | 5 | 1 | 80 | 5 | 100 |
| F12 (DQ) | 5 | 5 | 1 | 80 | 4 | 80 |
| F15 (DQ) | 5 | 5 | 1 | 80 | 5 | 100 |

Note:
PQ: primaquine;
DQ: decoquinate

Figure 18:
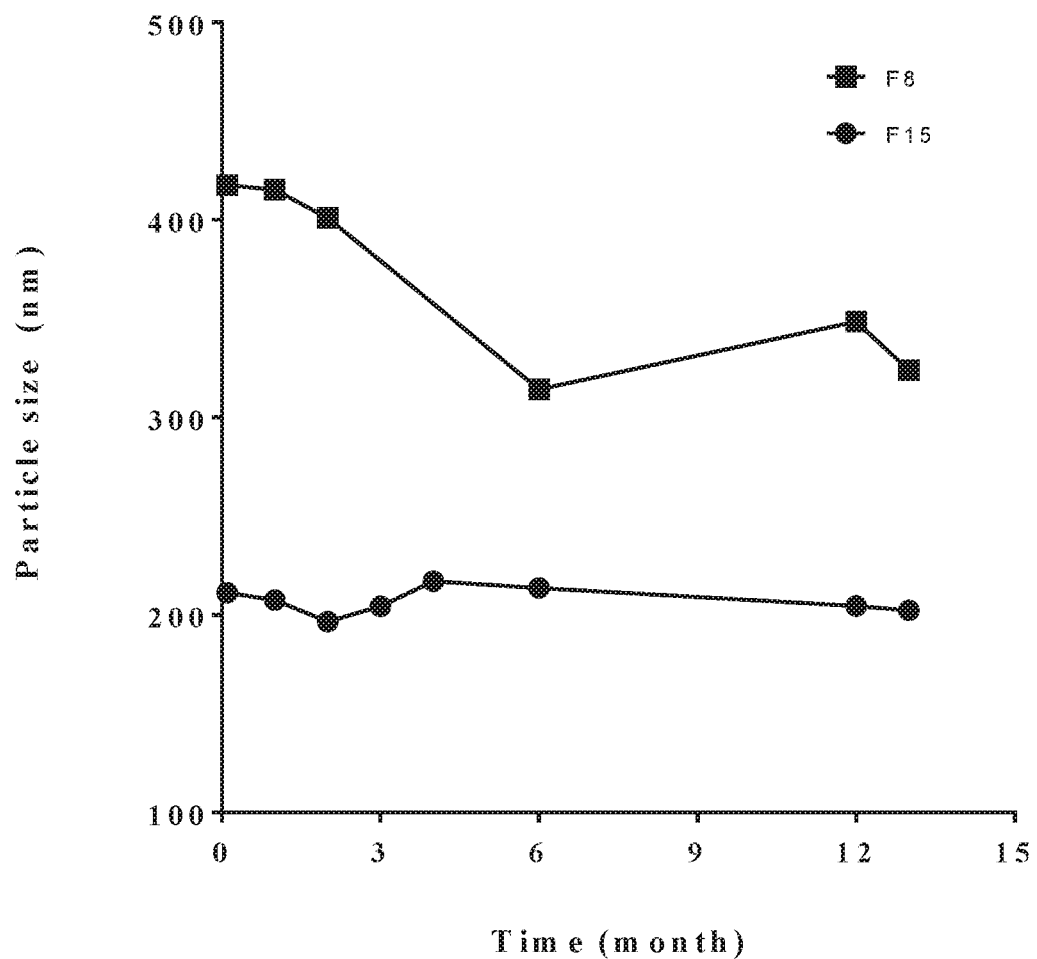
FIG. 18 illustrates the stability of nanoparticles created in Examples 8 (F8) and 15 (F15) by the HME method. The products from the HME machine were automatically dried after being exposed to room temperature and cooled to a solid before being pulverized to powder and then suspended in aqueous solutions. The sample suspensions remained in liquid form and kept at room temperature for 24 hours. An aliquot of each sample was taken, diluted in distilled water to the appropriate concentration and particles measured as shown in Table 4. The stock suspensions of F8 in PBS (pH 7.4) and F15 in saline solution (slightly acidic) were stored at room temperature for more than 12 months and observed periodically for stability of the particles in the aqueous phase.

Table 9 shows the data summary of mean particle size and polydispersity index (PDI) of F8 and F15 from multiple measurements corresponding to the points of FIG. 18. The data show that the particles in these formulations were relatively stable and the particle distributions remained homogeneous as indicated by PDI for more than 12 months.

TABLE 9

| Time (month) | F8 PS (nm) | F8 PDI | F15 PS (nm) | F15 PDI |
|---|---|---|---|---|
| 0.1 | 417.60 | 0.15 | 211.30 | 0.17 |
| 1 | 415.30 | 0.18 | 207.50 | 0.27 |
| 2 | 401.00 | 0.13 | 196.70 | 0.15 |
| 3 | | | 204.40 | 0.15 |
| 4 | | | 217.10 | 0.18 |
| 6 | 314.20 | 0.18 | 213.60 | 0.15 |
| 12 | | | 204.60 | 0.14 |
| 13 | 348.50 | 0.17 | 202.30 | 0.17 |
| Mean | 379.32 | 0.16 | 207.19 | 0.17 |
| SD | 40.81 | 0.02 | 6.39 | 0.04 |

Note:
PS: particle size;
PDI: polydispersity Index;

The applicant declares that the present application illustrates the product, the application, and the mode of the application of the present invention by above-described examples, but the present invention is not limited to the above-described detailed applications and the mode of the application, that is, it does not mean that the present invention must be carried out by relying upon the above-described detailed applications and the mode of the application. Those skilled in the pharmaceutical industry field should be aware that any modification of the invention, equivalents of the ingredients of the product of the invention, the addition of auxiliary ingredients, selection of specific modes, and the like are within the protection scope and the scope of disclosure of the present invention.

The invention claimed is:

1. A composition containing decoquinate, a hot-melt extrudable excipient and a plasticizer or a solubilizer,
    wherein the hot-melt extrudable excipient is selected from the group consisting of hydroxypropyl methylcellulose, hydroxypropyl methylcellulose acetate succinate, dimethylaminoethyl methacrylate copolymer, and a combination thereof,
    wherein the plasticizer or solubilizer is a poloxamer,
    wherein the hydroxypropyl methylcellulose acetate succinate has acetate substitution from 5% to 14% and succinate substitution from 4% to 14%.

2. The composition according to claim 1, wherein said composition comprises, by dry weight, 5% to 30% of decoquinate, 60% to 90% of hot-melt extrudable excipients, 5% to 10% of a plasticizer or a solubilizer.

3. The composition according to claim 1, wherein said decoquinate has molecular weight 418 g/mol.

4. The composition according to claim 1, wherein said hydroxypropyl methylcellulose has molecular weight range from 80 kDa to 550 kDa.

5. The composition according to claim 1, wherein said dimethylaminoethyl methacrylate copolymer has the weight average molar mass (Mw) approximately 47,000 g/mol.

6. The composition according to claim 1, wherein said poloxamer is poloxamer 188.

7. A thermal heat process for preparing a composition according to claim 1, comprising the steps of mixing decoquinate with a hot-melt extrudable excipient, a plasticizer or solubilizer to form a mixture; processing said mixture in a twin-screw extruder with multiple temperature zones at a hot-melt temperature less than the degradation temperature of decoquinate; and extruding said mixture to form an extrudate, wherein said decoquinate in said extrudate is in a solid solution.

8. The preparation process according to claim 7, wherein processing said mixture is carried out in a hot melt extruder at the hot melt temperature 50 to 200° C., preferably 120 to 180° C.

9. The preparation process according to claim 8, wherein the hot melt extruder is a twin-screw extruder wherein the screw rotation speed is 15 to 300 rpm, more preferably 25 to 150 rpm.

10. The preparation process according to claim 7, wherein processing said mixture in a twin-screw extruder to form an extrudate wherein said extrudate is in the state of solid dispersion or solid solution, preferably solid solution.

11. The preparation process according to claim 7, wherein said solid solution provides a therapeutic drug active and can be further fabricated as solid oral dosage forms to release the therapeutic drug in vivo to prevent or treat malarial infection or other parasitic disease or disorders.

12. A method for treating a disease, comprising administering to a subject in need thereof the composition of claim 1, wherein the disease is caused by a *Plasmodium* parasite.

13. The method of claim 12, wherein the disease is any one or more of *Plasmodium vivax*, *Plasmodium falciparum*, *Plasmodium malariae*, *Plasmodium ovale* and *Plasmodium*

*knowlesi*, preferably, *Plasmodium vivax, Plasmodium falciparum* and *Plasmodium ovale*.

* * * * *